United States Patent
Herscovici et al.

(10) Patent No.: US 6,812,218 B2
(45) Date of Patent: Nov. 2, 2004

(54) LIPID DERIVATIVES OF POLYTHIOUREA

(75) Inventors: Jean Herscovici, Paris (FR); Daniel Scherman, Paris (FR); Isabelle Tranchant, Paris (FR); Nathalie Mignet, Paris (FR); Christian Girard, Paris (FR)

(73) Assignee: Gencell S.A., Vitry-sur-Seine (FR)

( * ) Notice: Subject to any disclaimer, the term of this patent is extended or adjusted under 35 U.S.C. 154(b) by 179 days.

(21) Appl. No.: 10/143,751

(22) Filed: May 14, 2002

(65) Prior Publication Data

US 2003/0065033 A1 Apr. 3, 2003

Related U.S. Application Data

(60) Provisional application No. 60/297,482, filed on Jun. 13, 2001.

(51) Int. Cl.[7] ............................................... A61K 31/713

(52) U.S. Cl. ..................... 514/44; 514/476; 514/580; 435/458

(58) Field of Search ......................... 514/44, 476, 580; 435/458

(56) References Cited

U.S. PATENT DOCUMENTS 3,917,449 A * 11/1975 Wells et al. ................... 8/495

* cited by examiner

*Primary Examiner*—James Ketter
(74) *Attorney, Agent, or Firm*—Finnegan, Henderson, Farabow, Garrett & Dunner, L.L.P.

(57) ABSTRACT

The present invention relates to novel compounds which make it possible to transfer nucleic acids into cells. These novel compounds are lipid derivatives of polythiourea. They are useful for the in vitro, ex vivo or in vivo transfection of nucleic acids into various cell types.

58 Claims, 12 Drawing Sheets

Efficiency of transfection of HeLa cells with lipoplexes based on DTTU

LIPID DERIVATIVES OF POLYTHIOUREA

The application claims the benefit of U.S. Provisional Application No. 60/297,482, filed Jun. 13, 2001, and claims the right to priority based on French Patent Application No. 0106330, filed May 14, 2001, and the contents of both applications are incorporated herein by reference.

BACKGROUND OF THE INVENTION

The present invention relates to novel compounds which make it possible to transfer nucleic acids into cells. More precisely, these novel compounds are lipid derivatives of polythiourea. They are useful for the in vitro, ex vivo or in vivo transfection of nucleic acids into various cell types.

With the development of biotechnology, the possibility of effectively transferring nucleic acids into cells has become a necessity. It may involve the transfer of nucleic acids into cells in vitro, for example, for the production of recombinant proteins, or in the laboratory for studying the regulation of the expression of genes, the cloning of genes, or any other manipulation involving DNA. It may also involve the transfer of nucleic acids into cells in vivo, for example for the creation of transgenic animals, the production of vaccines, labeling studies or also therapeutic approaches. It may also involve the transfer of nucleic acids into cells ex vivo, in approaches including bone marrow transplants, immunotherapy or other methods involving the transfer of genes into cells collected from an organism for the purpose of their subsequent readministration.

Several methods have been proposed for the intracellular delivery of exogenous genetic material. One of them, in particular, is based on the use of nonviral vectors which constitute a highly advantageous alternative to the viral methods which are not completely risk free. These synthetic vectors have two main functions: to complex and to compact the nucleic acid to be transfected, and to promote its passage across the plasma membrane and possibly across the nuclear envelope.

Several families of synthetic vectors have thus been developed, such as for example polymers or alternatively biochemical vectors (consisting of a cationic protein combined with a cellular receptor ligand), but a major advance has in particular been made with the development of lipofectants and more particularly of cationic lipids. It has thus been demonstrated that cationic lipids, because of their overall positive charge, spontaneously interfere with DNA which is globally negative, forming nucleolipid complexes capable both of protecting the DNA against nucleases and of binding to the cellular membranes for intracellular release of the DNA.

Various types of cationic lipids have been synthesized to date: lipids comprising a quaternal ammonium group (for example DOTMA, DOTAP, DMRIE, DLRIE, and the like), lipopolyamines such as for example DOGS, DC-Chol or alternatively the lipopolyamines disclosed in Patent Application WO 97/18185, lipids combining both a quaternary ammonium group and a polyamine such as DOSPA, or alternatively lipids comprising various other cationic entities, in particular amidinium groups (for example ADPDE, ADODE or the lipids of patent application WO 97/31935).

However, the use of these cationic lipids as transfection agent still poses numerous problems, and their efficiency remains to be improved. In particular, it has been observed that to obtain efficient and stable nucleolipid complexes, it is in general necessary for these complexes to be highly cationic. However, it would be desirable to be able to have available vectors which are not cationic so as to form, with the nucleic acid, particles which are globally neutral or negative. Indeed, it has been observed that the globally cationic complexes formed between the nucleic acid and the cationic lipids tend to be captured by the reticuloendothelial system, which induces their elimination. In addition, the plasma proteins tend to become adsorbed at their surface because of the overall positive charge of the complexes formed, and this results in a loss of the transfection power. Furthermore, in a context of local injection, the presence of a large overall positive charge prevents the diffusion of the nucleic acid complexes away from the site of administration because the complexes become adsorbed onto the extracellular matrices; the complexes can therefore no longer reach the target cells, which consequently causes, a decrease in the transfer efficiency in relation to the injected quantity of complexes. Finally, it has also been observed, in many instances, that cationic lipids have an inflammatory effect.

BRIEF SUMMARY OF THE INVENTION

The object of the present invention is precisely to provide novel transfecting compounds which are innovative by virtue of their polythiourea functional group and which are capable of being efficiently used for the in vitro, ex vivo or in vivo transfection of nucleic acids. These novel compounds are particularly advantageous because:

the absence of positive charges from their structure makes it possible to solve the many problems raised by the use of cationic vectors discussed above, just like cationic lipids, they are capable of complexing and compacting nucleic acids and of promoting their transfection.

A first subject of the present invention is thus transfecting compounds characterized in that they consist of a polythiourea part linked to a lipid via a spacer.

In particular, the subject of the present invention is transfecting compounds of general formula (I):

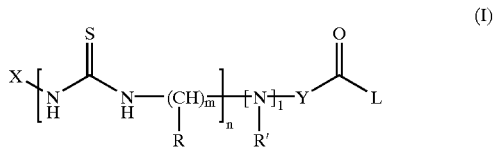

(I)

in which:

l is an integer chosen from 0 and 1, n is an integer chosen from 1, 2, 3, 4, 5 and 6, m is an integer chosen from 2, 3 and 4, it being possible for m to take different values within the different groups —[NH—CS—NH—(CH)$_m$]—, R' represents a group of general formula (II):

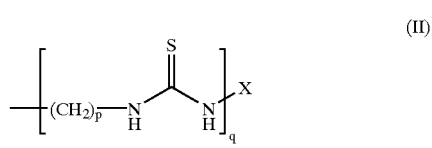

(II)

in which q is an integer chosen from 1, 2, 3, 4, 5 and 6, and p is an integer chosen from 2, 3 and 4, it being possible for p to take different values within the different groups —[(CH$_2$)$_p$—NH—CS—NH]—, R represents either a hydrogen atom or a group of general formula (II) as defined above, it being understood that when n is 1 and l is 0, then at least one group R is of formula (II), X, in the formulae (I) and (II), represents a saturated or unsaturated, linear or cyclic aliphatic group, comprising 1 to 8 carbon atoms, a mercaptomethyl (—$CH_2SH$) group, or alternatively a hydrophilic chain chosen from the groups:

—$(CH_2)_x$—$(CHOH)_u$—H with x an integer chosen from 1 to 10 and u an integer chosen from 1, 2, 3, 4, 5 and 6, or alternatively, —$(OCH_2CH_2O)_v$—H with v an integer chosen from 1, 2 and 3, it being understood that no more than one substituent X, both in the formulae (I) and (II), represents a hydrophilic chain, Y represents a spacer, and L represents:

either a group —$N(R_1)R_2$ with $R_1$ and $R_2$ which represent, independently of each other, a hydrogen atom or alternatively a fatty aliphatic chain, or alternatively a group of formula —$(CH_2)_t$—OZ with t representing an integer chosen from 11, 12, 13, 14 or 15 and Z represents a sugar, a polyol or a PEG, it being understood that at least one of $R_1$ and $R_2$ is different from hydrogen, or a group —$OR_3$, with $R_3$ which represents a steroid derivative.

According to the present invention, the term "spacer" is understood to mean any chemical group which makes it possible both to provide the linkage between the polythiourea part and the lipid part of the molecule, and to keep these two parts apart so as to attenuate any undesirable interruption between them. Preferred spacers may for example consist of one or more chemical functional groups chosen from alkyls having 1 to 6 carbon atoms, ketone, ester, ether, amide, amidine, carbamate or thiocarbamate functional groups, glycerol, urea, thiourea, or else aromatic rings. For example, the spacer may be chosen from the groups of formula:

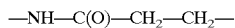

or:

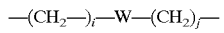

in which i and j are integers chosen between 1 and 6 inclusive and W is a group chosen from ketone, ester, ether, amide, amidine, carbamate or thiocarbamate functional groups, glycerol, urea, thiourea, or alternatively aromatic rings.

For the purposes of the present invention, the expression "fatty aliphatic chains" is understood to mean alkyl groups containing 10 to 22 carbon atoms which are saturated or unsaturated and optionally containing one or more heteroatoms, provided that said fatty aliphatic chains exhibit lipid properties. Preferably, they are linear or branched alkyl groups containing 10 to 22 carbon atoms and 1, 2 or 3 unsaturations. Preferably, said alkyl groups comprise 10, 12, 14, 16, 18, 20 or 22 carbon atoms. There may be mentioned more particularly the aliphatic groups —$(CH_2)_{11}CH_3$, —$(CH_2)_{13}CH_3$, $(CH_2)_{15}CH_3$ and —$(CH_2)_{17}CH_3$.

The term "sugar" is understood to mean, for the purposes of the invention, any molecule consisting of one or more saccharides. There may be mentioned, by way of example, sugars such as pyranoses and furanoses, for example glucose, mannose, rhamnose, galactose, fructose or alternatively maltose, lactose, saccharose, sucrose, fucose, cellobiose, allose, laminarabiose, gentiobiose, sophorose, melibiose, and the like. Preferably, the sugar(s) are chosen from glucose, mannose, rhamnose, galactose, fructose, lactose, saccharose and cellobiose. Furthermore, it may also involve so-called "complex" sugars, that is to say several sugars which are covalently coupled to each other, each sugar being preferably chosen from the list cited above. As suitable polysaccharides, there may be mentioned dextran, α-amylose, amylopectin, fructans, mannans, xylans and arabinans. Some preferred sugars may in addition interact with the cell receptors, such as for example certain types of lectin.

According to the invention, the term "polyol" is also understood to mean any linear, branched or cyclic hydrocarbon molecule comprising at least two hydroxyl functional groups. There may be mentioned by way of example glycerol, ethylene glycol, propylene glycol, tetritols, pentitols, cyclic pentitols (or quercitols), hexitols such as mannitol, sorbitol, dulcitols, cyclic hexitols or inositols, and the like (Stanek et al., The Monosaccharides Academic Press, pp. 621–655 and pp. 778–855). According to a preferred aspect; the polyols are chosen from the alcohols of general formula:

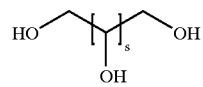

for which s is chosen from 2, 3, 4, 5 and 6.

When the compounds of general formula (I) according to the invention contain a polyethylene glycol (PEG) group, the latter generally comprises between 2 and 120 —$OCH_2CH_2O$— units, and preferably between 2 and 80 —$OCH_2CH_2O$— units. This may include simple PEGs, that is to say whose chain ending ends with a hydroxyl group, or else PEG whose terminal group is chosen from alkyls, for example methyl.

For the purposes of the present invention, the expression "steroid derivatives" is understood to mean polycyclic compounds of the cholestane type. These compounds may be natural or otherwise and are more preferably chosen from cholesterol, cholestanol, 3-α-5-cyclo-5-α-cholestan-6-β-ol, cholic acid, cholesteryl formate, chotestanyl formate, 3α,5-cyclo-5α-cholestan-6β-yl formate, cholesterylamine, 6-(1, 5-dimethylhexyl)-3a,5a-dimethylhexadecahydrocyclopenta[a]cyclopropa[2,3]cyclopenta[1,2-f]naphthalen-10-ylamine, or cholestanylamine.

According to a preferred variant of the invention, the transfecting compounds have the general formula (III):

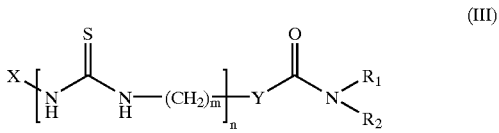

(III)

in which X, m, n and Y are as defined above in general formula (I), with the exception of n which is different from 1, and $R_1$ and $R_2$ represent, independently of each other, a hydrogen atom or else a fatty aliphatic chain, it being understood that at least one of $R_1$ and $R_2$ is different from hydrogen.

More preferably still, the transfecting compounds of the invention have the general formula (IV):

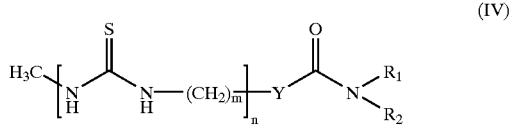

(IV)

in which m, n and Y are as defined above in general formula (I), with the exception of n which is different from 1, and $R_1$ and $R_2$ represent, independently of each other, a hydrogen atom or else a fatty aliphatic chain, it being understood that at least one of $R_1$ and $R_2$ is different from hydrogen.

It is understood that the present invention also relates to the isomers of the products of general formula (I) when they exist, as well as mixtures thereof.

The preparation of the compounds of general formula (I) according to the present invention is carried out using the following steps, in the order presented or according to any other known and equally suitable variant, using conventional organic synthesis techniques, in solution or on solid supports, which are well known to a person skilled in the art:

1) Production of the Lipid Part L

When the lipid part L of the compounds of general formula (I) is represented by a group —$N(R_1)R_2$ with $R_1$ and/or $R_2$ which represent a fatty aliphatic chain, the amine of formula $HN(R_1)R_2$ is first of all formed. Said amine may be obtained by condensing a carboxylic acid and an amine, one containing the substituent $R_1$ and the other the substituent $R_2$, to form the corresponding amide, followed by reduction of said amide thus obtained.

Amide formation is advantageously carried out by mixing constituents and melting, by heating at a temperature of greater than the melting point of the substances involved, in general between 20° C. and 200° C., followed by elimination of the water produced by dehydrating the medium; or more advantageously in the presence of a desiccating agent such as for example phosphorus pentoxide or any other substance which can absorb water. The formation of this intermediate amide may also be carried out using a variant of this method or another method for forming an amide (such as for example peptide-coupling type) involving carboxylic acids or derivatives thereof, and varying conditions and reagents [R. C. Larock, *Comprehensive Organic Transformations*, VCH Publishers] well known to a person skilled in the art.

The reduction of the amide previously obtained to an amine of formula $HN(R_1)R_2$ may be carried out for example using a reducing agent such as lithium aluminum hydride, or any other hydride or reducing agent effective in this case. The procedure is then preferably carried out in an aprotic solvent (for example tetrahydrofuran or ethers) at a temperature below the boiling point of the solvent or under a dry and/or inert atmosphere.

According to another variant, the lipid part designated as $HN(R_1)R_2$ may be commercially available.

When $R_1$ and/or $R_2$ represent(s) a group of formula —$(CH_2)_r$—OZ, the procedure is carried out as described above for forming the alkyl part, followed by simple coupling with a commercial PEG, polyol or sugar according to conventional techniques known to a person skilled in the art.

When the lipid part L of the compounds of the general formula (I) is represented by a group —$OR_3$, the latter is preferably chosen from commercially available products.

2) Grafting of the Spacer Y

The spacer Y is then attached to the lipid part L obtained in the preceding stage according to conventional techniques known to a person skilled in the art. According to a preferred variant, an amide bond is made by N-acylation of the lipid part L in an appropriate solvent such as dichloromethane, chloroform, tetrahydrofuran, or any other ether, at a temperature below the boiling point of the solvent, and under a dry and/or inert atmosphere. This reaction is preferably carried out in the presence of an amine-containing base such as N,N-dimethylaminopyridine, or in the presence of this base mixed with non-nucleophilic amine-containing bases such as triethylamine or else ethyl diisopropylamine. Pyridine may also be used, alone or mixed with another base, diluted with one of the solvents mentioned or used itself as solvent.

3) Formation of the Polythiourea Chain

The third part of the synthesis of the compounds of general formula (I) consists in the successive introduction of the thiourea units. This will be carried out in a series of reactions which may be repeated as many times as necessary in order to obtain the desired polythiourea part. According to a preferred method, the procedure is carried out in the following manner:

A) There is first of all grafted onto the Y—C(O)—L obtained in the preceding stage the first part of the unit in the form of a member —HN—$(CHR)_m$— group. For that, the procedure is advantageously carried out starting with a diamine-containing member of formula $H_2N$—$(CHR)_m$—$NH_2$ in the presence of a coupling agent, for example 1-benzotriazolyloxytris(pyrrolidino)phosphonium hexafluorophosphate (PyBOP), 1-benzotriazolyloxytris(dimethylamino)phosphonium hexafluorophosphate (BOP), O-(1H-benzotriazol-1-yl)-N,N,N',N'-tetramethyluronium hexafluorophosphate or tetrafluoroborate (HBTU or TBTU), dicyclohexylcarbodiimide (DCC), 1-(3-dimethylaminopropyl)-3-ethylcarbodiimide hydrochloride (EDC), or else 1-(3-trimethylammoniopropyl)-3-ethylcarbodiimide iodide, supported or otherwise. This coupling is carried out in a suitable solvent, for example dichloromethane, chloroform, tetrahydrofuran or any other ether, at a temperature below the boiling point of a solvent, and under a dry and/or inert atmosphere. The procedure is also carried out in the presence of a non-nucleophilic amine-containing base, for example ethyldiisopropylamine, triethylamine or else triisopropylamine. If the nature of the lipid part and of the spacer is compatible, a sequence of the SCN—$(CHR)_m$— type, or a precursor, may be grafted, thus making it possible to continue the synthesis through a stage such as that described below in C), B) The product obtained in the preceding stage is then converted, according to a preferred technique, to isothiocyanate by treating with carbon disulfide ($CS_2$), or with any other reagent known to the person skilled in the art for obtaining such a functionality [H. Ulrich, *Chemistry and Technology of Isocyanates*, Wiley (1996). *The Chemistry of Cyanates and their Thio Derivatives*, S. Patai Ed., Wiley (1977). S. Ozaki, *Recent Advances in Isocyanate Chemistry, Chem. Rev.* 72, 457 (1972)]. The reaction is advantageously carried out in a solvent such as for example tetrahydrofuran, or any other compatible ether solvent, at a temperature varying between that of the cooling mixtures and about 20° C. The procedure is also carried out in the presence of an agent capable of promoting the reaction and/or of trapping the hydrogen sulfide released during the reaction, for example dicyclohexylcarbodiimide (DCC).

C) The thiourea unit is then formed from the isothiocyanate obtained in the preceding stage so as to allow, where appropriate, the introduction of another segment of formula —$(CHR)_m$—. Advantageously, a diamine of formula $H_2N$—$(CHR)_m$—$NH_2$, optionally protected, is reacted, in its neutral form or in the form of an acid salt, with the isothiocyanate obtained in the preceding stage. This reaction is optionally carried out in the presence of a non-nucleophilic amine-containing base, for example triethylamine, ethyldiisopropylamine, triisopropylamine or else 1,8-diazabicyclo[5.4.0]undec-7-ene (DBU). The procedure is preferably carried out in a suitable solvent such as dichloromethane, chloroform, tetrahydrofuran or any other compatible ether or solvent, at a temperature which may be between that of the cooling mixtures and the reflux temperature of the solvent.

Stages B) and C) described above are then repeated sequentially and in the required order until the desired structure is obtained, so as to introduce the desired unit in n copies. To obtain branched structures, the procedure is carried out in a similar manner by introducing, at the appropriate time, the molecule(s) required to obtain a substitution R as described by formula (II).

4) Ending of the Polythiourea Part by Introducing the Substituent X

The last stage allowing the ending of the polythiourea-type chain(s) consists in introducing the substituent X. For that, conventional grafting methods known to a person skilled in the art, chosen according to the nature of the substituent X, are used. For example, when X represents an alkyl, the procedure is carried out by reacting an alkyl isothiocyanate, in the presence, when necessary, of a non-nucleophilic amine-containing base such as for example triethylamine, ethyldiisopropylamine, triisopropylamine or else 1,8-diazabicyclo[5.4.0]undec-7-ene (DBU). The reaction is performed in a suitable solvent, for example dichloromethane, chloroform, tetrahydrofuran or any other compatible ether or solvent, at a temperature between the temperature of the cooling mixtures and the reflux temperature of the solvent.

Naturally, when the various substituents can interfere with the reaction, it is preferable to protect them beforehand with compatible radicals which can be put in place and removed without affecting the remainder of the molecule. For that, the procedure is carried out according to conventional methods known to a person skilled in the art, and in particular according to the methods described in T. W. Greene, *Protective Groups in Organic Synthesis,* Wiley-Interscience, in McOmie, *Protective Groups in Organic Chemistry,* Plenum Press, or in P. J. Kocienski, *Protecting Groups,* Thieme.

Moreover, each stage of the method of preparation may be followed, where appropriate, by stages for separating and purifying the compound obtained according to any method known to a person skilled in the art.

Preferred compounds according to the present invention are:

The 3-(2-{3-[2-(3-{2-[3-(ditetradecylcarbamoyl) propionylamino]ethyl}thioureido)ethyl]thioureido}ethyl)-1-methylthiourea, designated herein as DTTU or as DT-3TU, corresponds to the general formula (I), wherein X=—CH$_3$; m=2; R=H; n=3; l=0; Y=NH—CO—CH$_2$—CH$_2$; and L=—N(R$_1$)R$_2$ où R$_1$=R$_2$=C$_{14}$H$_{29}$. Designation of this compound as DT-3TU, refers to the three thiourea groups comprised therein; in addition, examples of this nomenclature include, DT-4TU comprising four thioureas, DT-2TU comprising two thioureas, etc.

The 3-(2-{3-[2-(3-{2-[3-(2-{3-[ditetradecyl-carbamoyl] propionylamino}-ethyl)-thioureido]-ethyl}-thioureido)-ethyl]-thioureido}-ethyl)-1-methylthiourea or DT-4TU is according to the general formula (I), wherein X=—CH3; m=2; R=H; n=4; and l==0; Y=NH—CO—CH$_2$—CH$_2$; and L=—N(R$_1$)R$_2$ where R$_1$=R$_2$=C$_{14}$H$_{29}$.

The DT-3TU diol or Synthesis of [2-(3-{2-[3-(2-{3-[2-(3-(ditetradecyl-carbamoyl)propionylamino)-ethyl]-thioureido}ethyl)-thioureido]-ethyl}-thioureido)-ethyl]-propane-1,2-diol, is according to the general formula (I), wherein:

$$X = \quad HO \diagup \diagdown OH$$

m=2
R=H
n=3
l=0
Y=NH—CO—CH$_2$—CH$_2$; and
L=—N(R$_1$)R$_2$ where R$_1$=R$_2$=C$_{14}$H$_{29}$.

The DT-2TU diol or [2-(3-{2-[3-(ditetradecyl-carbamoyl) propionylamino]-ethyl}-thioureido)-ethyl]-propane-1,2-diol Where according to the general formula (I), wherein $$X = \quad HO \diagup \diagdown OH$$

m=2
R=H
n=2
l=0
Y=NH—CO—CH$_2$—CH$_2$; and
L=—N(R$_1$)R$_2$ where R$_1$=R$_2$=C$_{14}$H$_{29}$ Another subject of the invention relates to the compositions comprising a transfecting compound according to the invention and a nucleic acid. The respective quantities of each component may be easily adjusted by a person skilled in the art according to the transfecting compound used, the nucleic acid and the desired applications (in particular the type of cells to be transfected).

For the purposes of the invention, the expression "nucleic acid" is understood to mean both a deoxyribonucleic acid and a ribonucleic acid. They may be natural or artificial sequences, and in particular genomic DNA (gDNA), complementary DNA (cDNA), messenger RNA (mRNA), transfer RNA (tRNA), ribosomal RNA (rRNA), hybrid sequences such as DNA/RNA chimeroplasts or synthetic or semisynthetic sequences, and oligonucleotides which are modified or otherwise. These nucleic acids may be of human, animal, plant, bacterial or viral origin and the like. They may be obtained by any technique known to persons skilled in the art, and in particular by the screening of libraries, by chemical synthesis or by mixed methods including the chemical or enzymatic modification of sequences obtained by the screening of libraries. They may be chemically modified. In general, they contain at least 10, 20, 50 or 100 consecutive nucleotides, and preferably at least 200 consecutive nucleotides. More preferably still, they contain at least 500 consecutive nucleotides.

As regards more particularly deoxyribonucleic acids, they may be single- or double-stranded, as well as short oligonucleotides or longer sequences. In particular, the nucleic acids advantageously consist of plasmids, vectors, episomes, expression cassettes and the like. These deoxyribonucleic acids may carry a prokaryotic or eukaryotic replication origin which is functional or otherwise in the target cell, one or more marker genes, sequences for regulating transcription or replication, genes of therapeutic interest, anti-sense sequences which are modified or otherwise, regions for binding to other cellular components, and the like.

Preferably, the nucleic acid comprises one or more genes of therapeutic interest under the control of regulatory sequences, for example one or more promoters and a transcriptional terminator which are active in the target cells.

For the purposes of the invention, the expression gene of therapeutic interest is understood to mean in particular any gene encoding a protein product having a therapeutic effect. The protein product thus encoded may in particular be a protein or a peptide. This protein product may be exogenous, homologous or endogenous in relation to the target cell, that is to say a product which is normally expressed in the target cell when the latter has no pathological condition. In this case, the expression of a protein makes it possible, for example, to palliate an insufficient expression in the cell or the expression of a protein which is inactive or weakly active because of a modification, or to overexpress said protein. The gene of therapeutic interest may also encode a mutant of a cellular protein, having increased stability, modified activity and the like. The protein product may also be heterologous in relation to the target cell. In this case, an expressed protein may, for example, supplement or provide an activity which is deficient in the cell, allowing it to combat a pathological condition, or to stimulate an immune response.

Among the therapeutic products for the purposes of the present invention, there may be mentioned more particularly enzymes, blood derivatives, hormones, lymphokines and cytokines as well as their inhibitors or their antagonists: interleukins, interferons, TNF, antagonists of interleukin 1, soluble receptors for interleukin 1 or TNFα, and the like (FR 92/03120), growth factors, neuro-transmitters or their precursors or synthesis enzymes, trophic factors (BDNF, CNTF, NGF, IGF, GMF, aFGF, bFGF, NT3, NT5, HARP/pleiotrophin and the like), apolipoproteins (ApoAI, ApoAIV, ApoE, and the like, FR 93/05125), dystrophin or a minidystrophin (FR 91/11947), the CFTR protein associated with cystic fibrosis, tumor suppressor genes (p53, Rb, Rap1A, DCC, k-rev, and the like, FR 93/04745), genes encoding factors involved in coagulation (Factors VII, VII, IX), the genes involved in DNA repair, suicide genes (thymidine kinase, cytosine deaminase), the genes for hemoglobin or other protein carriers, metabolic enzymes, catabolic enzymes and the like.

The nucleic acid of therapeutic interest may also be a gene or an anti-sense sequence or a DNA encoding an RNA with ribosome function, whose expression in the target cell makes it possible to control the expression of genes or the transcription of cellular mRNAs. Such sequences can, for example, be transcribed in the target cell into RNAs which are complementary to cellular mRNAs and thus block their translation to protein, according to the technique described in Patent EP 140 308. The therapeutic genes also comprise the sequences encoding ribozymes, which are capable of selectively destroying target RNAs (EP 321 201).

As indicated above, the nucleic acid may also comprise one or more genes encoding an antigenic peptide, which is capable of generating an immune response in humans or in animals. In this specific embodiment, the invention allows the production of vaccines or the carrying out of immunotherapeutic treatments applied to humans or to animals, in particular for treating or preventing infections, for example viral or bacterial infections, or cancerous states. They may be in particular antigenic peptides specific for the Epstein-Barr virus, the HIV virus, the hepatitis B virus (EP 185 573), the pseudo-rabies virus, the syncitia forming virus, other viruses, or antigenic peptides specific for tumors (EP 259 212).

Preferably, the nucleic acid also comprises sequences allowing the expression of the gene of therapeutic interest and/or the gene encoding the antigenic peptide in the desired cell or organ. They may be sequences which are naturally responsible for the expression of the gene considered when these sequences are capable of functioning in the infected cell. They may also be sequences of different origin (responsible for the expression of other proteins, or even synthetic). In particular, they may be promoter sequences of eukaryotic or viral genes. For example, they may be promoter sequences derived from the genome of the cell which it is desired to infect. Likewise, they may be promoter sequences derived from the genome of a virus. In this regard, there may be mentioned, for example, the promoters of the E1A, MLP, CMV and RSV genes, and the like. In addition, these expression sequences may be modified by the addition of activating or regulatory sequences, and the like. The promoter may also be inducible or repressible.

Moreover, the nucleic acid may also comprise, in particular upstream of the gene of therapeutic interest, a signal sequence directing the therapeutic product synthesized in the secretory pathways of the target cell. This signal sequence may be the natural signal sequence of the therapeutic product, but it may also be any other functional signal sequence, or an artificial signal sequence. The nucleic acid may also comprise a signal sequence directing the synthesized therapeutic product towards a particular compartment of the cell.

The compositions according to the invention may, in addition, comprise one or more adjuvants capable of combining with the transfecting compound/nucleic acid complexes and of improving the transfecting power thereof. In another embodiment, the present invention therefore relates to compositions comprising a nucleic acid, a transfecting compound as defined above and at least one adjuvant capable of combining with the transfecting compound/nucleic acid complexes and of improving the transfecting power thereof. The presence of this type of adjuvant (lipids, peptides, proteins or polymers for example) may make it possible advantageously to increase the transfecting power of the compounds. In this regard, the compositions of the invention may comprise, as adjuvant, one or more neutral lipids, which possess in particular the property of forming lipid aggregates. The term "lipid aggregate" is a generic term which includes liposomes of any type (both unilamellar and multilamellar) as well as micelles or else more amorphous aggregates.

More preferably, the neutral lipids used within the framework of the present invention are lipids containing two fatty chains. In a particularly advantageous manner, natural or synthetic lipids which are zwitterionic or lacking ionic charge under physiological conditions are used. They may be chosen more particularly from dioleoylphosphatidylethanolamine (DOPE), oteoylpalmitoyl-phosphatidylethanolamine (POPE), di-stearoyl, -palmitoyl, -myristoylphosphatidyl-ethanolamines as well as their derivatives which are N-methylated 1 to 3 times, phosphatidylglycerols, diacylglycerols, glycosyldiacylglycerols, cerebrosides (such as in particular galactocerebrosides), sphingolipids (such as in particular sphingomyelins) or asialogangliosides (such as in particular asialoGM1 and GM2). Advantageously, the lipid adjuvants used in the context of the present invention are chosen from DOPE, DOPC or cholesterol.

These different lipids may be obtained either by synthesis or by extraction from organs (for example the brain) or from eggs, by conventional techniques well known to persons skilled in the art. In particular, the extraction of the natural lipids may be carried out by means of organic solvents (see also Lehninger, Biochemistry).

Preferably, the compositions of the invention comprise from 0.01 to 20 equivalents of adjuvants for one equivalent of nucleic acid in mol/mol and, more preferably, from 0.5 to 5 molar equivalents.

According to another alternative, the adjuvants mentioned above making it possible to improve the transfecting power of the compositions according to the present invention, in particular the peptides, proteins or certain polymers, such as polyethylene glycol, may be conjugated with the transfecting compounds according to the invention, and not simply mixed. In this case, they are covalently linked either to the substituent X in the general formula (I), or to the end of the alkyl chain(s) $R_1$ and/or $R_2$ when the latter are fatty aliphatic chains. It is also advantageous to use as adjuvant, a polyethylene glycol covalently linked to cholesterol (chol-PEG). In effect, when such adjuvant is used with transfectant compositiosn according to the present invention, resulting particles have a smaller size, thereby decreasing aggregation thereof, and increasing their half-life in the blood circulation. Amount of transfectant DT-3TU used according to the present invention is such that particles have a size inferior to 500 nm. Preferred amount of DT-3TU used is at least equal to 40 nmol of lipids DT-3TU/µg of DNA (See Examples 11, 13, and 14 herein below).

According to a particularly advantageous embodiment, the compositions of the present invention comprise, in addition, a targeting element which makes it possible to orient the transfer of the nucleic acid. This targeting element may be an extracellular targeting element which makes it possible to orient the transfer of the nucleic acid toward certain cell types or certain desired tissues (tumor cells, hepatic cells, hematopoietic cells and the like). It may also be an intracellular targeting element which makes it possible to orient the transfer of the nucleic acid toward certain preferred cellular compartments (mitochondria, nucleus and the like). The targeting element may be mixed with the transfecting compounds according to the invention and with the nucleic acids, and in this case, the targeting element is preferably covalently linked to a fatty alkyl chain (at least 10 carbon atoms) or to a polyethylene glycol. According to another alternative, the targeting element is covalently linked to the transfecting compound according to the invention either at the level of the substituent X or on the spacer Y, or else at the end of $R_1$ and/or $R_2$ when the latter represent fatty aliphatic chains. Finally, the targeting element may also be linked to the nucleic acid as was specified above.

Among the targeting elements which may be used within the framework of the invention, there may be mentioned sugars, peptides, proteins, oligonucleotides, lipids, neuromediators, hormones, vitamins or derivatives thereof. Preferably, they are sugars, peptides, vitamins or proteins such as for example antibodies or antibody fragments, ligands of cell receptors or fragments thereof, receptors or receptor fragments. For example, they may be ligands of growth factor receptors, cytokine receptors, cellular lectin-type receptors, folate receptors, or RGD sequence-containing ligands with an affinity for the receptors for adhesion proteins such as the integrins. There may also be mentioned the receptors for transferin, HDLs and LDLs, or the folate transporter. The targeting element may also be a sugar which makes it possible to target lectins such as the receptors for asialoglycoproteins or for sialydes, such as the Sialyl Lewis X, or alternatively an Fab fragment of antibodies, or a single-chain antibody (ScFv).

The subject of the invention is also the use of the transfecting compounds as defined above for transferring nucleic acids into cells in vitro, in vivo or ex vivo. More precisely, the subject of the present invention is the use of the transfecting compounds according to the invention for the preparation of a medicament intended for treating diseases, in particular diseases resulting from a deficiency in a protein or nucleic product. The polynucleotide contained in said medicament encodes said protein or nucleic product, or constitutes said nucleic product, capable of correcting said diseases in vivo or ex vivo.

For uses in vivo, for example in therapy or for studying the regulation of genes or the creation of animal models of pathological conditions, the compositions according to the invention can be formulated for administration by the topical, cutaneous, oral, rectal, vaginal, parenteral, intranasal, intravenous, intra-muscular, subcutaneous, intraocular, transdermal, intratracheal or intraperitoneal route, and the like. Preferably, the compositions of the invention contain a vehicle which is pharmaceutically acceptable for an injectable formulation, in particular a direct injection into the desired organ, or for administration by the topical route (on the skin and/or the mucous membrane). They may be in particular isotonic sterile solutions, or dry, in particular freeze-dried, compositions which, upon addition, depending on the case, of sterilized water or of physiological saline, allow the constitution of injectable solutions. The nucleic acid doses used for the injection as well as the number of administrations may be adapted according to various parameters, and in particular according to the mode of administration used, the relevant pathological condition, the gene to be expressed, or the desired duration of treatment. As regards more particularly the mode of administration, it may be either a direct injection into the tissues, for example at the level of the tumors, or an injection into the circulatory system, or a treatment of cells in culture followed by their reimplantation in vivo by injection or transplantation. The relevant tissues within the framework of the present invention are, for example, the muscles, skin, brain, lungs, liver, spleen, bone marrow, thymus, heart, lymph, blood, bones, cartilages, pancreas, kidneys, bladder, stomach, intestines, testicles, ovaries, rectum, nervous system, eyes, glands, connective tissues, and the like.

Another subject of the present invention relates to a method of transferring nucleic acids into cells comprising the following steps:
(1) bringing the nucleic acid into contact with a transfecting compound according to the present invention, to form a complex, and
(2) bringing the cells into contact with the complex formed in (1).

The invention relates, in addition, to a method of treating the human or animal body comprising the following steps:
(1) bringing the nucleic acid into contact with a transfecting compound according to the present invention, to form a complex, and
(2) bringing the cells of the human or animal body into contact with the complex formed in (1).

The cells may be brought into contact with the complex by incubating the cells with said complex (for uses in vitro or ex vivo), or by injecting the complex into an organism (for uses in vivo). In general, the quantity of nucleic acid intended to be administered depends on numerous factors such as for example the disease to be treated or to be prevented, the actual nature of the nucleic acid, the strength of the promoter, the biological activity of the product expressed by the nucleic acid, the physical condition of the individual or of the animal (weight, age and the like), the mode of administration and the type of formulation. In general, the incubation is preferably carried out in the presence, for example, of 0.01 to 1000 µg of nucleic acid per $10^6$ cells. For administration in vivo, nucleic acid doses ranging from 0.01 to 50 mg may for example be used. The administration may be carried out as a single dose or repeated at intervals.

In the case where the compositions of the invention contain, in addition, one or more adjuvants as defined above, the adjuvant(s) may be mixed beforehand with the transfecting compound according to the invention and/or the nucleic acid. Alternatively, the adjuvant(s) may be administered before the administration of the nucleolipid complexes.

According to another advantageous alternative, the tissues may be subjected to a chemical or physical treatment intended to improve the transfection. In the case of the physical treatment, the latter may use electrical pulses as in the case of electrotransfer, or else mechanical forces as in the case of sodoporation.

The present invention thus provides a particularly advantageous method for transferring nucleic acids in vivo, in particular for the treatment of diseases, comprising the in vivo or in vitro administration of a nucleic acid encoding a protein or which can be transcribed into a nucleic acid capable of correcting said disease, said nucleic acid being combined with a transfecting compound according to the invention under the conditions defined above.

The transfecting compounds of the invention are particularly useful for transferring nucleic acids into primary cells or into established lines. They may be fibroblast cells, muscle cells, nerve cells (neurons, astrocytes, glial cells), hepatic cells, hematopoietic cells (lymphocytes, CD34, dendritic cells, and the like), epithelial cells and the like, in differentiated or pluripotent form (precursors).

Another subject of the present invention also relates to the transfection kits which comprise one or more transfecting compounds according to the invention and/or mixtures thereof. Such kits may be provided in the form of a packaging which is compartmented so as to receive various containers such as for example vials or tubes. Each of these containers comprises the various elements necessary to carry out the transfection, individually or mixed: for example one or more transfecting compounds according to the invention, one or more nucleic acids, one or more adjuvants, cells, and the like.

In addition to the preceding arrangements, the present invention also comprises other characteristics and advantages which will emerge from the examples and figures below, which should be considered as illustrating the invention without limiting its scope. In particular, the applicant proposes, without limitation, an operating protocol as well as reaction intermediates which may be used to prepare the transfecting compounds according to the invention. Of course, it is within the capability of persons skilled in the art to draw inspiration from this protocol or intermediate products to develop similar methods so as to arrive at these same compounds.

ABBREVIATIONS USED

EtBr: ethidium bromide
DCC: dicyclohexylcarbodiimide
DPPC: 1,2-dipalmitoyl-sn-glycero-3-phosphocholine
DTTU: 3-(2-{3-[2-(3-{2-[3-(ditetradecylcarbamoyl) propionylamino]-ethyl}thioureido)ethyl] thioureido}ethyl)-1-methylthiourea (also designated DT-3TU)
EPC: L-α-phosphatidylcholine 95% (egg)
PyBOP: benzotriazol-1-yloxytripyrrolidinophosphonium hexafluorophosphate
TBE: tris-borate-EDTA
TFA: trifluoroacetic acid
THF: tetrahydrofuran

The y-axis represents the expression of luciferase in RLU/µg of protein.

The x-axis indicates the quantity of DTUU (in nmol) per µg of DNA.

Figure 6:
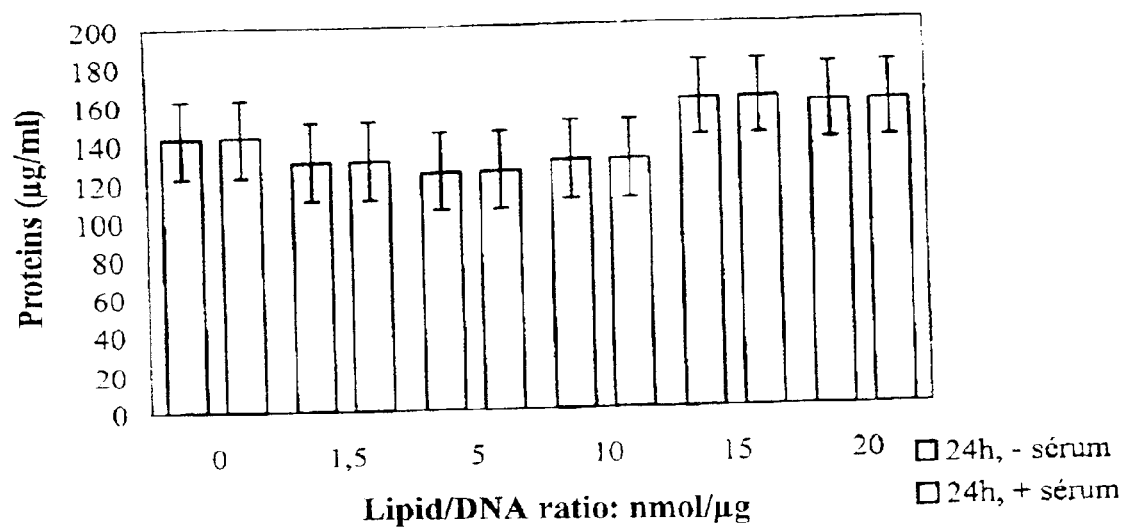

FIG. 6: Level of proteins (as absorbance) of HeLa cells not treated or treated with EPC+DTTU/DNA liposomes at various lipid/DNA ratios in nmol/µg.

Figure 7:
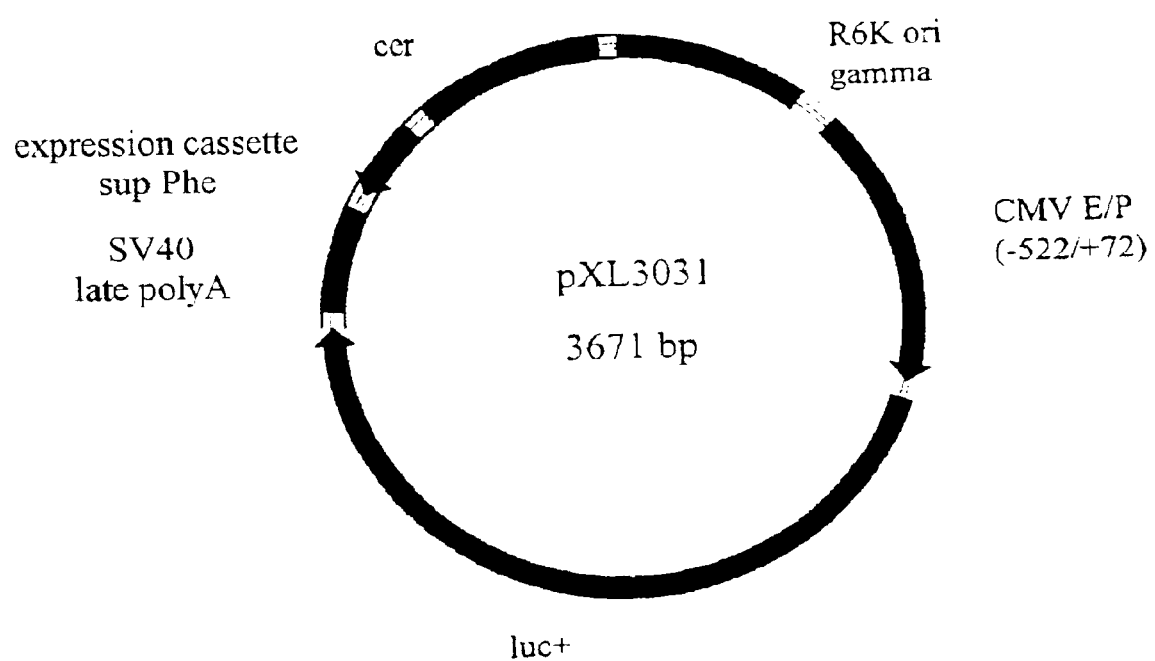

FIG. 7: Schematic representation of the plasmid pXL3031.

Figure 8:

FIG. 8: Agarose gel (0.8%/TBE) showing the compaction of the plasmid pXL3031 (µg) as a function of the quantity of DT-3TU/DPPC nanoemulsions (nmol) used.

Figure 9:
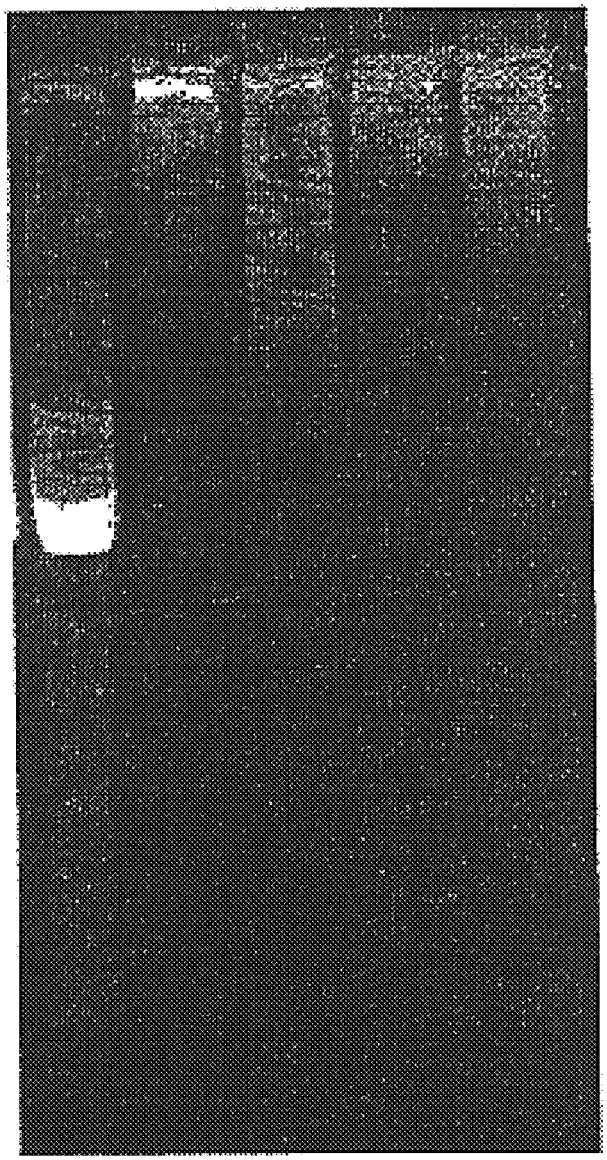

FIG. 9: Agarose gel (0.8%/TBE) showing the compaction of the plasmid pXL3031 (µg) as a function of the quantity of DT-3TU/DPPC/chol-PEG nanoemulsions (nmol) used.

Figure 10:
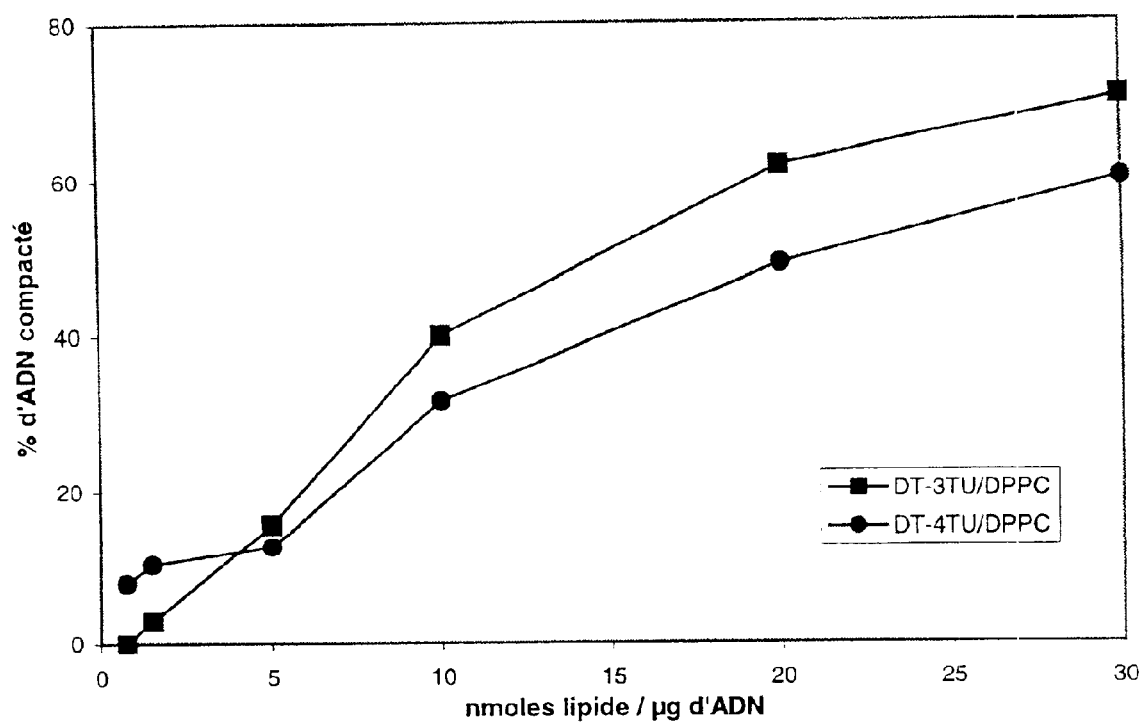

FIG. 10: Variation of the percentage of DNA compacted as a function of the quantity of DT-4TU/DPPC mixture (in nmol) per µg of nucleic acid in comparison with various amount of DT-3TU/DPPC (in nmol) per µg of nucleic acid.

Figure 11:
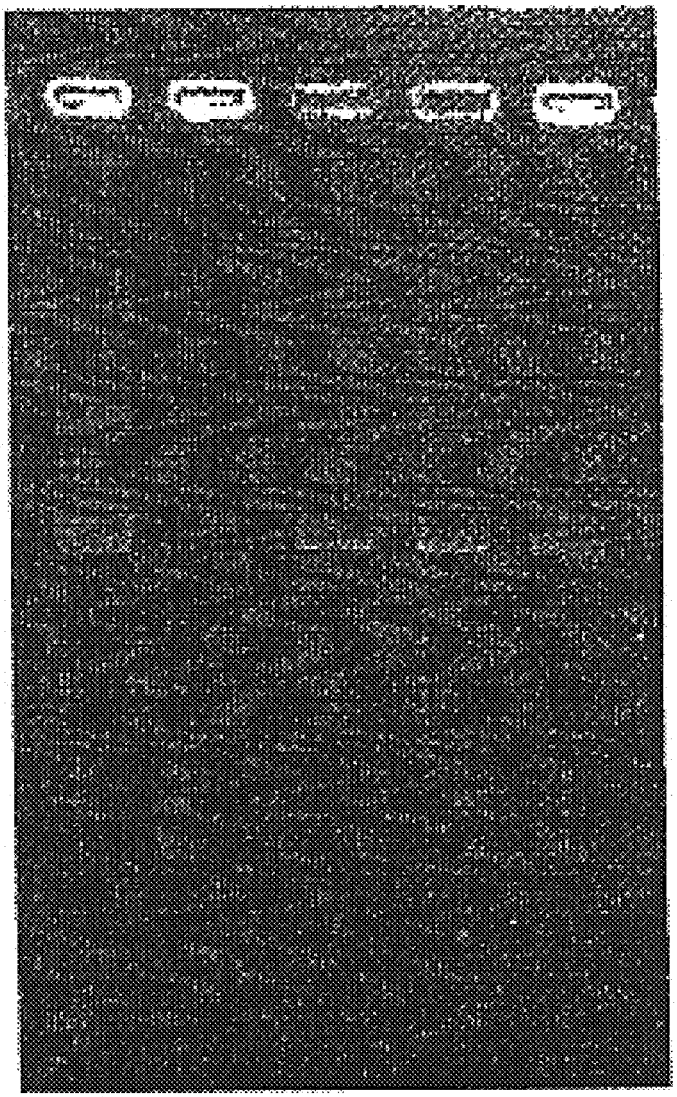

FIG. 11: Agarose gel (0.8%/TBE) showing the protection by the DT-3TU/DPPC mixture of the plasmid pXL3031 (µg) against DNAses degradation.

Figure 12:
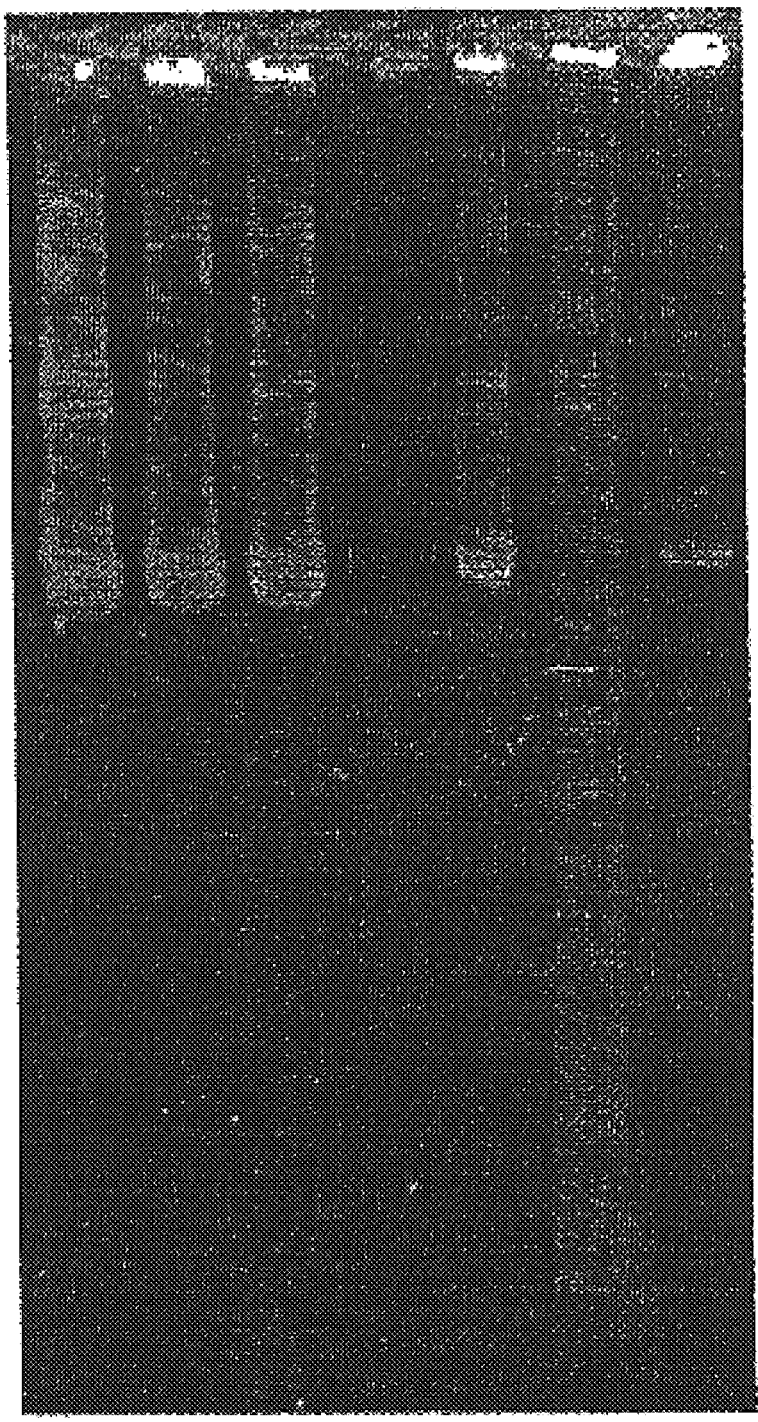

FIG. 12: Agarose gel (0.8%/TBE) showing the protection by the DT-3TU/DPPC mixture of the plasmid pXL3031 (µg) when placed in serum. Lane 1 corresponds to DNA; lanes 2 and 3 correspond to DNA alone or in presence of 10 nmol/µg of DT-3TU/DPPC nanoemulsions in 150 mM of NaCl, and in 20% of serum (lanes 4 and 5), and in 100% of serum (lanes 6 and 7).

Figure 13:
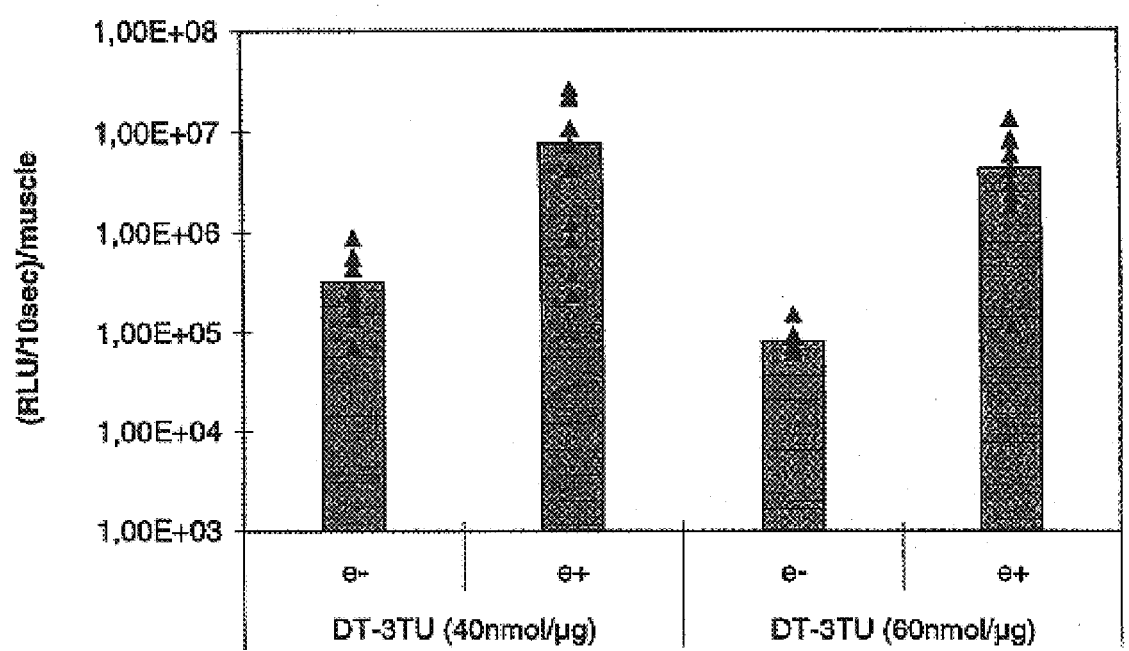

FIG. 13: Efficiency of in vivo muscle transfection by complexes of DNA and liposomes DT-3TU/DPPC, present in various amounts of lipids/DNA in nmol/µg with or without electrotransfert (e−/e+).

Figure 14:
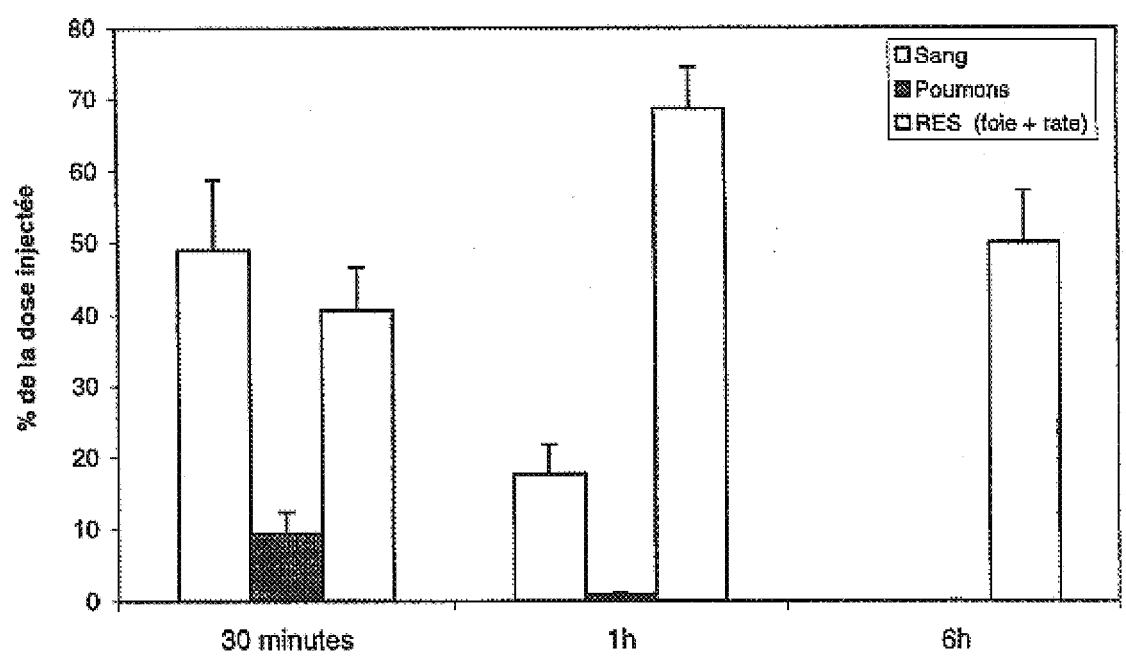

FIG. 14: In vivo biodistribution of complexes DT-3TU/DPPC/DOPE-Rh/DNA in mouse, after 30 min, 1 h, and 6 h in blood, lungs and RES (liver and spleen). This figure shows that the particles have the property of being furtive: 50% of the complexes are retrieved in the blood circulation after 30 min.

DETAILED DESCRIPTION OF THE INVENTION

The present invention is illustrated by the following nonlimiting examples.

EXAMPLES

Customary reagents and catalysts such as triethylamine, trifluoroacetic acid, p-toluenesulfonic acid, benzotriazol-1-yloxytripyrrolidinophosphonium hexafluorophosphate (PyBOP), dicyclohexylcarbodiimide (DCC), carbon disulfide, tetradecylamine, di-tert-butyl dicarbonate, 4-dimethylaminopyridine, or diisopropylethylamine were commercially available.

The proton nuclear magnetic resonance ($^1$H NMR) spectra were recorded on Bruker 300, 400 and 600 MHz spectrometers. The chemical shifts were expressed in ppm (parts per million) and the multiplicities by the customary abbreviations.

In the text which follows, the nucleic acid used was the plasmid pXL3031 described in the publication Gene Therapy (1999) 6, pp. 1482–1488, which contained the luc gene encoding luciferase under the control of the cytomegalovirus CMV E/P promoter. This plasmid is represented in FIG. 7. Its size is 3671 bp. The plasmid solution used was diluted to 1.262 g/l in water for injection.

Example 1
Synthesis of DT-3TU

The 3-(2-{3-[2-(3-{2-[3-(ditetradecylcarbamoyl)propionylamino]ethyl}thioureido)ethyl]thioureido}ethyl)-1-methylthiourea, designated herein as DTTU, or DT-3TU, corresponds to the general formula (I), wherein X=—CH$_3$; m=2; R=H; n=3; l=0; Y=NH—CO—CH$_2$—CH$_2$; and L=—N(R$_1$)R$_2$ or R$_1$=R$_2$=C$_{14}$H$_{29}$.

a) Synthesis of ditetradecylamide (1)

131.6 mmol of tetradecanoic acid (30 g) and 140.8 mmol of tetradecylamine (30 g) were mixed in a round-bottomed flask equipped with a magnetic stirrer connected to a collecting flask containing a drying agent (P$_2$O$_5$). The reaction mixture was then heated for 4 hours to 170° C. under reduced pressure (50 mmHg). The crude material was then solubilized in THF (700 ml; heated slightly in order to aid solubilization) and then 4 equivalents of Amberlyst-15 resin (8 g) were added in order to bind the excess amine. After stirring for 20 minutes, the solution was filtered and the filtrate was then concentrated to give 55.11 g of a white solid (yield: 99%).

$^1$H NMR (CDCl$_3$): δ (ppm) 0.88 (t, 6H, J=6.5 Hz, —CH$_3$), 1.25 (m, 42 H, —CH$_2$—, 1.47 (m, 2H, CO—CH$_2$—CH$_2$), 1.60 (m, 2H, N—CH$_2$—CH$_2$), 2.15 (t, 2H, J=7.5 Hz, CO—CH$_2$), 3.23 (dt, 2H, J=7 Hz, N—CH$_2$), 5.50 (s, 1H, NH).

$^{13}$C NMR (CDCl$_3$): δ (ppm) 14.09 (C$_{14}$+C'$_{13}$), 22.71 (C$_{13}$+C'$_{12}$), 25.90 (C'$_2$), 26.99 (C$_3$), 29.69 (—CH$_2$—), 31.96 (C$_{12}$+C'$_{11}$), 36.97 (C'$_1$), 39.56 (C$_1$), 160 (CO).

b) Synthesis of ditetradecylamine (2)

47 mmol of ditetradecylamide (20 g) were dissolved in 700 ml of anhydrous THF, under nitrogen, in a round-bottomed flask equipped with a condenser and a drying tube. The mixture was cooled to 0° C. and then 89 mmol of lithium aluminum hydride LiAlH$_4$ (3.4 g) were added. After addition, the mixture was then heated under reflux for 5 hours, with vigorous stirring. Once the reaction was complete, the mixture was cooled to 0° C. in order to carry out the hydrolysis by successive addition of 3.4 ml of water, 6.8 ml of 1N sodium hydroxide and 3.4 ml of water. After stirring for 1 hour at room temperature, the crude reaction material was filtered on a Büchner funnel and the filtrate was concentrated. The product obtained was then purified on 1.5 equivalents of A-15 resin (15 g) in 300 ml of THF, with stirring for 30 minutes. The resin was filtered and redissolved in 300 ml of THF, with addition of 2 equivalents of triethylamine (19.2 ml). After stirring for 30 minutes, the solution was filtered and the filtrate was concentrated to give 17.72 g of a white solid (yield: 92%).

$^1$H NMR (CDCl$_3$): δ (ppm) 0.87 (t, 6H, J=6.5 Hz, —CH$_3$), 1.25 (m, 44 H, —CH$_2$—), 1.46 (m, 4H, N—CH$_2$—CH$_2$), 2.58 (t, 4H, J=7 Hz, N—CH$_2$).

$^{13}$C NMR (CDCl$_3$): δ (ppm) 14.06 (C$_{14}$), 22.69 (C$_{13}$), 27.48 (C$_3$), 28.29 (C$_2$), 29.69 (C$_4$-C$_{11}$), 31.96 (C$_{12}$), 50.15 (C$_1$).

c) Synthesis of N,N-ditetradecylsuccinamic acid (3)

12.65 mmol of succinic anhydride (1.266 g), 12.65 mmol of 4-dimethylaminopyridine (1.546 g) and 10.75 mmol of ditetradecylamine (4.407 g) were successively added to 125 ml of dichloromethane in a round-bottomed flask. The reaction mixture was stirred for 18 hours at room temperature. Once the reaction was complete, the mixture was extracted with dichloromethane and hydrochloric acid (1N). The organic phase was then washed with brine and dried over magnesium sulfate, filtered and then concentrated to give 4.21 g of product (3) (yield: 66%).

$^1$H NMR (CDCl$_3$): δ (ppm) 0.85 (t, 6H, J=6.3 Hz, —CH$_3$), 1.23 (m, 44 H, —CH$_2$—), 1.48 (m, 4H, N—CH$_2$—CH$_2$), 2.64 (s, 4H, CO—CH$_2$—CH$_2$—CO), 3.22 (m, 4H, N—CH$_2$).

$^{13}$C NMR (CDCl$_3$): δ (ppm) 14.08 (C$_{14}$), 22.69 (C$_{13}$), 27.74 (C$_3$), 28.10 (CO—CH$_2$—CH$_2$—CO), 28.92 (C$_2$), 29.67 (C$_4$-C$_{11}$), 30.07 (CO—CH$_2$—CH$_2$—CO), 31.95 (C$_{12}$), 46.21 and 47.98 (C$_1$), 4171.46 (CO—NHH(C$_{14}$H$_{29}$)$_2$), 173.14 (NH—CO).

d) Synthesis of the tert-butyl ester of 2-aminoethylcarbamic acid (4)

18.6 mmol of di-tert-butyl dicarbonate (4 g) were added dropwise to 102.83 mmol of ethylenediamine (6.17 g) in solution in chloroform (20 ml), under nitrogen. The reaction mixture was then stirred for 18 hours at room temperature. Once the reaction was complete, the solution was concentrated. The resulting oil, dissolved in dichloromethane, was washed with a saturated aqueous sodium carbonate solution. The organic phase was then dried over magnesium sulfate, filtered and concentrated. The crude product was purified by flash chromatography (dichloromethane/methanol 9:1). 2.38 g of product (4) were thus obtained (yield: 80%).

$^1$H NMR (CDCl$_3$): δ (ppm) 1.40 (s, 9H, (CH$_3$)$_3$), 1.52 (s, 2H, NH$_2$), 2.59 (t, 2H, J=5.9 N—CH$_2$), 3.12 (q, 2H, $^4$J=5.4 Hz, NHBoc-CH$_2$), 5.1 (s,1H, NHBoc)

¯C NMR (CDCl$_3$): δ (ppm) 28.15 (CH$_3$)$_3$, 41.67 (CH$_2$—NHBoc), 43.46 (CH$_2$—NH$_2$), 78.31 (C—(CH$_3$)$_3$, 156.21 (C=O).

e) Synthesis of the tert-butyl ester of 2-[3-(ditetradecylcarbamoyl)propionylamino]ethylcarbamic acid (5)

8.84 mmol of PyBOP (4.601 g), 9.72 mmol of the amine (4) obtained in the preceding stage (1.558 g) and 24.31 mmol of diisopropylethylamine (4.24 ml) were successively added to a solution of 8.84 mmol of the acid (3) obtained above (4.5 g) in 88 ml of dichloromethane. The solution was then stirred for 4 hours at room temperature. At the end of the reaction, the reaction mixture was filtered and then the product was purified by flash chromatography (heptane/ethyl acetate 5:5 and then heptane/ethyl acetate 2:8). 3.79 g of the ester (5) were thus obtained (yield: 66%).

$^1$H NMR (CDCl$_3$): δ (ppm) 0.87 (t, 6H, J=6.6 Hz, —CH$_3$), 1.25 (m, 44H, —CH$_2$—), 1.43 (s, 9H, (CH$_3$)$_3$) 1.48 (m, 4H, N—CH$_2$—CH$_2$), 2.56 (t, 2H, J=6.7 Hz, CH$_2$3), 2.69 (t, 2H, J=6.2 Hz, CH$_2$4), 3.28 (m, 4H, N—CH$_2$), 3.3 (m, 4H, CH$_2$1+CH$_2$2).

$^{13}$C NMR (CDCl$_3$): δ (ppm) 14.07 (C"$_{14}$), 22.56 (C"$_{13}$), 26.99 ((CH$_3$)$_3$), 27.73 (C"$_3$), 28.29 (C'$_2$), 28.59 (C"$_2$), 29.27 (C"$_4$–C"$_{11}$), 29.55 (C'$_3$), 31.41 (C"$_{12}$), 39.85 (C$_2$), 40.39 (C$_1$), 46.21 and 47.98 (C"$_1$), 78.77 (C(IV)-Boc), 156.33 (CO-Boc), 171.46 (CO—NH(C$_{14}$H$_{29}$)$_2$), 173.14 (C'$_1$).

f) Synthesis of 2-[3-(ditetradecylcarbamoyl)propionylamino]ethylamine (6)

12.2 mmol of distilled TFA (0.94 ml) were added to 2.44 ml of the ester (5) obtained in the preceding stage (1.59 g). After two hours, the reaction was complete. The product was coevaporated twice with cyclohexane in a rotary evaporator in the cold state. The yield was quantitative.

$^1$H NMR (CDCl$_3$): δ (ppm) 0.91 (t, 6H, J=6.6 Hz, —CH$_3$), 1.29 (m, 44H, —CH$_2$—), 1.51 (m, 4H, N—CH$_2$—CH$_2$), 2.59 (t, 2H, J=6.7 Hz, H'$_3$), 2.71 (t, 2H, J=6.2 Hz, H'$_3$), 3.29 (m, 4H, N—CH$_2$), 3.31 (m, 4H, H$_1$, H$_2$).

$^{13}$C NMR (CDCl$_3$): δ (ppm) 14.00 (C"$_{14}$), 22.67 (C'$_{13}$), 27.35 (C'$_3$), 27.95 (C'$_2$), 28.53 (C$_2$), 29.65 (C"$_4$–C"$_{11}$), 30.70 (C'$_3$), 31.94 (C"$_{12}$), 37.83 (C$_2$), 40.08 (C$_2$), 47.85 and 49.42 (C"$_1$), 171.72 (CO—NH(C$_{14}$H$_{29}$)$_2$), 173.26 (C'$_1$).

g) Synthesis of ((1,1-dimethylethoxycarbonyl)amino)ethylisothiocyanate (7)

43.69 mmol of DCC (9.015 g), 297.9 mmol of carbon disulfide (17.9 ml) in 27.5 ml of THF were successively added to a round-bottomed flask. The mixture was cooled to −7° C. with a bath of ice and ammonium chloride NH$_4$Cl (4/1). 43.69 mmol of the amine (4) obtained above (7 g) dissolved in 20.5 ml of anhydrous THF were then added dropwise over 30 minutes. The mixture was allowed to return to room temperature and the mixture was kept stirring for 21 hours. After evaporation, diethyl ether was added to precipitate the dicyclohexylurea formed. The solution was filtered, the filtrate was concentrated and then purified by flash chromatography (heptane/ethyl/acetate 80:20) to give 6.357 g of desired product (7) (yield: 72%).

$^1$H NMR (CDCl$_3$): δ (ppm) 1.38 (s, 9H, (CH$_3$)$_3$), 3.31 (q, 2H, $^4$J=5.8 Hz, NHBoc-CH$_2$), 3.59 (t, 2H, J=5.6 Hz, S=C=N—CH$_2$), 5.16 (s, 1H, NHBoc)

$^{13}$C NMR (CDCl$_3$): δ (ppm) 28.54 ((CH$_3$)$_3$), 41.03 (CH$_2$)—NHBoc), 45.53 (CH$_2$—N=C=S), 79.71 (C—(CH$_3$)$_3$, 132.72 (C=S), 156.21 (C=O).

h) Synthesis of the tert-butyl ester of 2-(3-{2-[3-(ditetradecylcarbamoyl)propionylamino]ethyl}thioureido)ethylcarbamic acid (8)

9.76 mmol of triethylamine (1.36 ml) were directly added to 2.44 mmol of the amine (6) obtained above (1.62 g) and the mixture was kept stirring for 15 minutes. 24.4 ml of dichloromethane and 2.92 mmol of the isothiocyanate (7) obtained in the preceding stage (0.59 g) were then added. The reaction mixture was stirred at room temperature for 12 hours. The mixture was then evaporated and then purified by flash chromatography (ethyl acetate/heptane 6:4 and then 100% of ethyl acetate). 1.343 g of the desired ester (8) were thus obtained (yield: 73%).

$^1$H NMR (CDCl$_3$): δ (ppm) 0.67 (t, 6H, J=6.4 Hz, —CH$_3$), 1.05 (m, 44 H, —CH$_2$—), 1.26 (s, 9H, CH$_3$)$_3$), 1.35 (m, 4H, N—CH$_2$—CH$_2$), 2.31 (m, 2H, H$^3$'$_3$), 2.49 (m, 2H, H$^3$'$_3$), 3.06 (m, 4H, N—CH$_2$), 3.11 (m, 4H, H$_1$, H"$_2$), 3.47 (m, 4H, H$_2$, H"$_1$), 7.14 (2H, H thiourea).

$^{13}$C NMR (CDCl$_3$): δ (ppm) 13.95 (C$^{4'}_{14}$), 22.57 (C$^{4'}_{13}$), 26.92 ((CH$_3$)$_3$), 27.07 ($^{4'}$C$_3$), 27.78 (C$^{3'}_2$), 28.39 (C$^{4'}$2), 28.82 (C$^{3'}_3$), 29.55 (C$^{4'}$4–C$^{4'}$11); 31.83 (C$^{4'}$12), 39.45 (C"$_2$), 43.63 (C$_2$ and C"$_1$), 46.39 and 48.16 (C$^{4'}_1$), 79.24 (C(IV)-Boc), 156.53 (CO-Boc), 171.72 (CO—NH(C$_{14}$H$_{29}$)$_2$), 173.71 (C$^{3'}_1$), 182.97 (C=S).

i) Synthesis of 2-(3-{2-[3-(ditetradecylcarbamoyl)-propionylamino]ethyl}thioureido)ethylamine (9)

9.86 mmol of distilled TFA (0.76 ml) were added to 1.98 mmol of the product (8) obtained in the preceding stage (1.5 g). After 3 hours, the reaction was complete. The product was coevaporated twice with cyclohexane using a rotary evaporator in the cold state. The yield was quantitative.

$^1$H NMR (CDCl$_3$): δ (ppm) 0.67 (t, 6H, J=6.4 Hz, —CH$_3$), 1.05 (m, 44 H, —CH$_2$—), 1.26 (s. 9H, CH$_3$)$_3$), 1.31 (m, 4H, N—CH$_2$—CH$_2$), 2.31 (m, 2H, H$^3$'$_3$), 2.49 (m, 2H, H$^3$'$_3$), 3.06 (m, 4H, N—CH$_2$), 3.11 (m, 4H, H$_1$, H"$_2$), 3.44 (m, 4H, H$_2$, H"$_1$), 7.10, (2H, H thiourea).

$^{13}$C NMR (CDCl$_3$): δ (ppm) 13.85 (C$^{4'}_{14}$), 22.49 (C$^{4'}_{13}$), 27.01 (C$^{4'}_3$), 27.72 (C$^{3'}_2$), 28.29 (C$^{4'}_2$), 28.79 (C$^{3'}_3$), 29.49 (C$^{4'}_4$–C$^{4'}_{11}$), 31.77 (C$^{4'}_{12}$), 39.42 (C"$_2$), 43.75 (C$_2$ and C"$_1$), 46.29 and 48.09 (C$^{4'}_1$), 171.72 (CO—NH(C$_{14}$H$_{29}$)$_2$), 173.71 (C$^{3'}_1$), 182.97 (C=S).

j) Synthesis of the tert-butyl ester of 2-{3-[2-(3-{2-[3-(ditetradecylcarbamoyl)propionylamino]ethyl}-thioureido)ethyl]thioureido}ethylcarbamic acid (10)

7.92 mmol of triethylamine (1.1 ml) were directly added to 1.98 mmol of the amine (9) obtained in the preceding stage (1.47 g) and the mixture was kept stirring for 15 minutes. 19.8 ml of dichloromethane and 2.38 mmol of the isothiocyanate (7) obtained above (0.461 g) were then added and the reaction was allowed to proceed at room temperature, with stirring, for 12 hours. The mixture was then evaporated and then purified by flash chromatography (ethyl acetate/heptane 6:4 and then ethyl acetate/methanol 98:2). 1.136 g of the desired product (10) were thus obtained (yield: 67%).

$^1$H NMR (CDCl$_3$): δ (ppm) 0.74 (t, 6H, J=6.6 Hz, —CH$_3$), 1.12 (m, 44 H, —CH$_2$—), 1.30 (s, 9H, CH$_3$)$_3$), 1.45 (m, 4H, N—CH$_2$—CH$_2$), 2.41 (m, 2H, H$^5$'$_2$), 2.58 (m, 2H, H$^5$'$_2$), 3.12 (m, 4H, N—CH$_2$), 3.25 (m, 4H, H$_1$, H$^{4'}_2$), 3.56 (m, 8H, H$_2$, H"$_1$, H"$_2$, H$^{4'}_1$), 7.14 (4H, H thiourea).

$^{13}$C NMR (CDCl$_3$): δ (ppm) 14.06 (C$^{6'}_{14}$), 22.57 (C$^{6'}_{13}$), 27.11 (C$^{6'}_3$), 26.93 ((CH$_3$)$_3$), 27.79 (C$^{5'}_2$), 28.38 (C$^{6'}_2$), 28.81 (C$^{5'}_3$), 29.56 (C$^{6'}_4$–C$^{6'}_{11}$), 31.83 (C$^{6'}_{12}$), 39.55 (C$^{4'}_2$), 43.66 (C$_2$, C"$_1$, C"$_2$, C$^{4'}_1$), 46.49 and 48.23 (C$^{6'}_1$) 79.28 (C(IV)-Boc), 156.61 (CO-Boc), 171.96 (CO—NH(C$_{14}$H$_{29}$)$_2$), 173.72 (C$^{5'}_1$), 182.93 (C=S).

k) Synthesis of 2-{3-[2-(3-{2-[3-(ditetradecyl-carbamoyl)propionylamino]ethyl}thioureido)ethyl]thioureido}ethylamine (11)

5.84 mmol of distilled TFA (0.45 ml) were added to 1.15 mmol of the product (10) obtained in the preceding stage (1 g). After 3 hours, the reaction was complete. The product was coevaporated twice with cyclohexane in a rotary evaporator in the cold state. The yield was quantitative.

$^1$H NMR (CDCl$_3$): δ (ppm) 0.85 (t, 6H, J=6.6 Hz, —CH$_3$), 1.25 (m, 40 H, —CH$_2$—), 1.48 (m, 4H, N—CH$_2$—CH$_2$), 1.52 (m, 4H, N—CH$_2$—CH$_2$—CH$_2$), 2.65 (m, 2H, H, H$^5$'$_2$), 2.77 (m, 2H, H$^5$'$_3$), 3.26 (m, 4H, N—CH$_2$), 3.43 (m, 4H, H$_1$, H$^{4'}_2$), 3.85 (m, 8H, H$_2$, H"$_1$, H"$_2$, H$^{4'}_1$), 7.44 (4H, H thiourea).

$^{13}$C NMR (CDCl$_3$): δ (ppm) 14.05 (C$^{6'}_{14}$), 22.68 (C$^{6'}_{13}$), 27.05 (C$^{6'}_3$), 27.58 (C$^{5'}_2$), 28.71 (C$^{6'}_2$), 29.36 (C$^{5'}_3$), 29.67 (C$^{6'}_4$–C$^{6'}_{11}$), 31.94 (C$^{6'}_{12}$), 40.49 (C$^{5'}_1$), 43.49 (C in α of C=S), 47.40 and 49.07 (C$^{6'}_1$), 172.16 (CO—NH(C$_{14}$H$_{29}$)$_2$), 174.00 (NH—CO), 182.73 (C=S).

I) Synthesis of DT-3TU (12)

1.12 mmol of triethylamine (0.16 ml) were directly added to 0.28 mmol of the amine (11) obtained in the preceding stage (0.24 g) and the mixture was kept stirred for 15 minutes. 2.8 ml of dichloromethane and 0.34 mmol of methyl isothiocyanate (0.024 g) were then added and the reaction was allowed to proceed at room temperature, with stirring for 12 hours. The mixture was then evaporated and then purified by HPLC (high-performance liquid chromatography) on a $C_4$ column with the following gradient: initially a water/methanol 95:5 mixture up to 100% of methanol. The product obtained was again purified on a small silica column (ethyl acetate/heptane 80:20 and then 100% of ethyl acetate). 118 mg of DTTU were thus obtained (yield: 51%).

$^1$H NMR (CDCl$_3$): δ (ppm) 0.86 (t, 6H, J=6.7 Hz, —CH$_3$—), 1.24 (m, 40 H, —CH$_2$—), 1.44 (m, 4H, N—CH$_2$—CH$_2$), 1.54 (m, 4H, N—CH$_2$—CH$_2$—CH$_2$), 2.52 (m, 2H, H$^{6'}_2$), 2.67 (m, 2H, H$^{6'}_2$), 3.05 (m, 3H, terminal —CH$_3$), 3.21 (m, 4H, N—CH$_2$), 3.32 (m, 2H, H$^{5'}_2$), 3.75 (m, 10H, H'$_1$, H'$_2$, H$^{3'}_1$, H$^{3'}_2$, H$^{5'}_1$), 7.14 (6H, H thiourea).

$^{13}$C NMR (CDCl$_3$): δ (ppm) 14.09 (C$^{7'}_{14}$), 22.69 (C$^{7'}_{13}$), 27.24 (C$^{7'}_3$), 27.89 (C$^{6'}_2$), 28.87 (C$^{7'}_2$), 29.38 (C$^{6'}_3$), 29.67 (C$^{7'}_4$–C$^{7'}_{11}$), 31.26 (terminal —CH$_3$), 31.94 (C$^{7'}_{12}$), 39.71 (C$^{5'}_2$), 43.63 (C'$_1$, C'$_2$, C$^{3'}_1$, C$^{3'}_2$, C$^{5'}_1$), 46.67 and 48.40 (C$^{7'}_1$), 172. 16 (CO—NH(C$_{14}$H$_{29}$)$_2$),174.00 (C$^{6'}_1$), 182.73 (C=S).

Example 2

Synthesis of DT-4TU

The 3-(2-{3-[2-(3-{2-[3-(2-{3-[ditetradecyl-carbamoyl]propionylamino}ethyl)-thioureido]-ethyl}-thioureido)-ethyl]-thioureido}-ethyl)-1-methylthiourea or DT-4TU was according to the general formula (I), wherein X=—CH$_3$; m=2; R=H; n=4; and l=0; Y=NH—CO—CH$_2$—CH$_2$; and L=—N(R$_1$)R$_2$ where R$_1$=R$_2$=C$_{14}$H$_{29}$.

For the synthesis of DT-4TU, amine (11) was used as the starting material.

a) Synthesis of the tert-butyl ester of 2-(3-{2-[3-(2-{3-[2-(3-(ditetradecyl-carbamoyl)propionylamino)-ethyl]-thioureido}-ethyl)-thioureido]-ethyl}-thioureido)ethyl carbamic acid (13)

Triethylamine (0.643 ml, 4.6 mmol) was added to the amine (11) (0.8 g, 0.92 mmol) and the mixture was kept under stirring for 15 minutes. Then, CH$_2$Cl$_2$ (9.2 ml) was added to the mixture followed by the addition of isothionate (7) (0.224 g, 1.104 mmol) and the reaction mixture was left to react at room temperature under stirring for 20 hours. The mixture was then evaporated and purified on column chromatography (ethyl acetate/heptane 8:2 followed by ethyl acetate/methanol 90:10); 252 mg of the desired were obtained (46% yield).

$^1$H NMR (CDCl$_3$): δ (ppm) 0.86 (t, 6H, J=6 Hz, H-14'), 1.25 (m, 44 H, H-4'–H-11'), 1.42 (s, 9H, CH$_3$)$_3$), 1.45 (m, 4H, H-2'), 2.55 (m, 2H, H-2), 2.69 (m, 2H, H-3), 3.22 (m, 4H, H-1'), 3.31 (m, 4H, H-5 et H-15), 3.74 (m, 12H, H-6, H-8, H-9, H-11, H-12, H-14), 7.31 (6H, H thiourea).

$^{13}$C NMR (CDCl$_3$): δ (ppm) 14.06 (C-14'), 22.66 (C-13'), 27.21 (C-3'), 27.88 (C-2), 28.50 ((CH$_3$)$_3$), 28.87 (C-2'), 29.64 (C-4'–C-11'), 31.27 (C-3), 31.92 (C-12'), 39.639 (C-5), 40.44 (C-13), 43.73 (C-6, C-8, C-9, C-11, C-12, C-14), 46.64 et 48.38 (C-1'), 79.10 (C-17), 156.63 (C-16), 172.35 (C-1), 174.04 (C-4), 182.65 (C-7, C-10, C-13).

b) Synthesis of 2-(3-{2-[3-(2-{3-[2-(3-(ditetradecyl-carbamoyl)propionylamino)-ethyl]-thioureido}-ethyl)-thioureido]-ethyl}-thioureido)-ethyl amine (14)

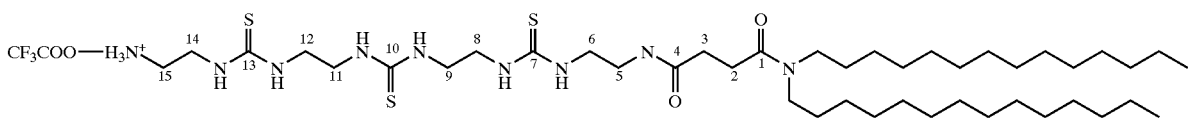

Distilled TFA (0.142 ml, 1.84 mmol) was added to the amine boc (13) obtained in the preceding stage (0.22 g, 0.23 mmol). After 6 hours the reaction was complete. The product was coevaporated twice with cyclohexane using a rotary evaporator in the cold state. The product was placed on sodium hydroxide in a dessicator overnight. The yield was quantitative.

$^1$H NMR (CDCl$_3$): δ (ppm) 0.74 (t, 6H, J=6.6 Hz, H-14'), 1.12 (m, 44 H, H-4'–H-11'), 1.45 (m, 4H, H-2'), 2.41 (m, 2H, H-2), 2.58 (m, 2H, H-3), 3.12 (m, 4H, H-1'), 3.25 (m, 4H, H-5 et H-15), 3.56 (m, 12H, H-6, H-8, H-9, H-11, H-12, H-14), 7.14 (6H, H thiourea).

$^{13}$C NMR (CDCl$_3$): δ (ppm) 14.06 (C-14'), 22.57 (C-13'), 27.11 (C-3'), 27.79 (C-2), 28.38 (C-2'), 28.81 (C-4'–C-11'), 29.56 (C-3), 31.83 (C-12'), 39.55 (C-5, C-9), 43.66 (C-6, C-8, C-9, C-11, C-12, C-14), 46.49 et 48.23 (C-1'), 171.96 (C-1), 173.72 (C-4), 182.93 (C-7, C-10, C-13).

c) Synthesis of 3-(2-{3-[2-(3-{2-[3-(2-{3-[ditetradecyl-carbamoyl]propionylamino}-ethyl)-thioureido]-ethyl}-thioureido)-ethyl]-thioureido}-ethyl)-1-methylthiourea (DT-4TU) (15)

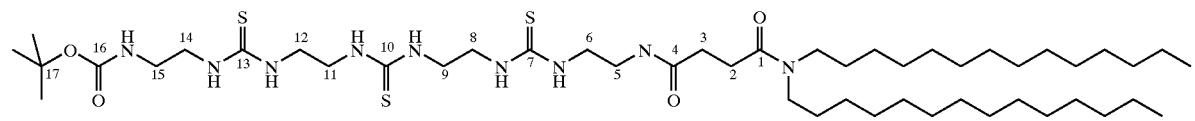

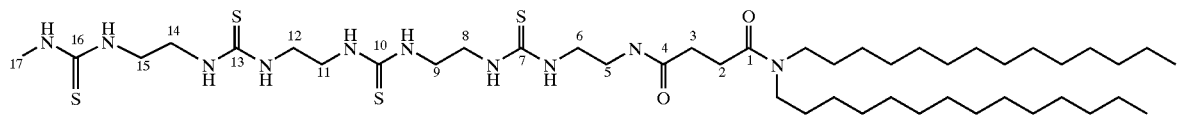

Triethylamine (1.38 mmol, 0.19 ml) was directly added to the amine (14) (0.23 mmol, 0.224 g) obtained in the preceding stage and the reaction mixture was kept under stirring for 15 minutes. Then, $CH_2Cl_2$ (2.3 ml) and methylisothiocyanate (0.46 mmol, 0.034 g) were added and the reaction mixture was left at room temperature under stirring for 12 hours. The mixture was then evaporated and purified by flash chromatography (100% ethyl acetate followed by ethyl acetate/methanol 95:5). 109 mg of DT-4TU were thus obtained (yield: 51%).

$^1$H NMR (CDCl$_3$): δ (ppm) 0.88 (t, 6H, J=6.3 Hz, H-14'), 1.26 (m, 44 H, H-4'–H-11'), 1.45 1.45 (m, 4H, H-2'), 1.58 (m, 4H, H-3'), 2.57 (m, 2H, H-2), 2.73 (m, 2H, H-3), 3.03 (m, 3H, H-17), 3.23 (m, 4H, H-1'), 3.31 (m, 2H, H-5), 3.73 (m, 14H, H-6, H-8, H-9, H-11, H-12, H-14, H-15), 7.14 (8H, H thiourea).

$^{13}$C NMR (CDCl$_3$): δ (ppm) 14.09 (C-14'), 22.69 (C-13'), 27.24 (C-3'), 27.89 (C-2), 28.87 (C-2'), 29.38 (C-3), 29.67 (C-4'–C-11'), 31.26 (C-17), 31.94 (C-12'), 39.71 (C-5), 43.63 (C-6, C-8, C-9, C-11, C-12, C-14, C-15), 46.67 et 48.40 (C-1'), 172.16 (C-1), 174.00 (C-4), 182.73 (C-7, C-10, C-13, C-16).

Example 3
Synthesis of DT-2TU diol

The DT-2TU diol or [2-(3-{2-[3-(ditetradecyl-carbamoyl) propionylamino]-ethyl}-thioureido)-ethyl]-propane-1,2-diol is defined according to the general formula (I), wherein

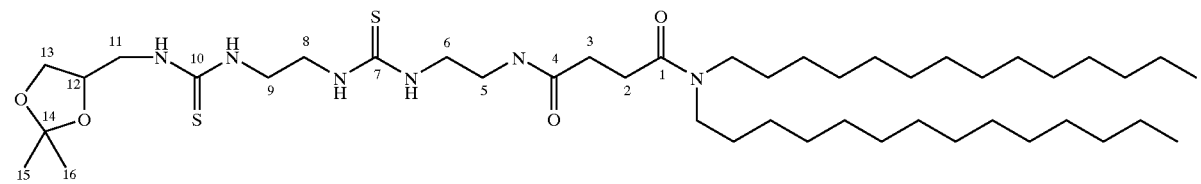

X =

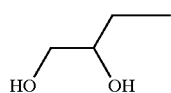

m=2

R=H n=2 l=0;

Y=NH—CO—CH$_2$—CH$_2$;

L=—N(R$_1$)R$_2$ where R$_1$=R$_2$=C$_{14}$H$_{29}$ a) Synthesis of 4-isothiocyanatomethyl-2,2-dimethyl-[1,3] dioxalane (16)

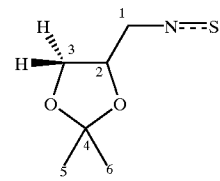

DCC (3.146 g, 15.25 mmol) and carbon disulfide (6.253 ml, 104.005 mmol) in THF (9.6075 mL) were successively added to a round-bottomed flask. The mixture was cooled to −7° C. using an ice/NH$_4$Cl (4:1) bath and 2,2-dimethyl-1, 2-dioxalane-4-methanamine (2 g, 15.25 mmol) dissolved in anhydrous THF (7.1675 mL) was added dropwise over 30 minutes. The reaction mixture was allowed to return to room temperature and was kept under stirring for 21 hours. After evaporation, diethyl ether was added. The mixture was filtered, evaporated and purified by chromatography.

$^1$H NMR (CDCl$_3$): δ (ppm) 1.33 et 1.44 (s, 3H, H-5, H-6), 3.57 (dd, 1H, J=4.8 Hz, J=1.44 Hz, H-1), 3.69 (dd, 1H, J=4.9 Hz, J=1.44 Hz, H-1'), 3.80 (dd, 1H, J=5.4 Hz et J=8.7 Hz, H-3), 4.09 (dd, 1H, J=6.3 Hz, et J=8.7 Hz, H-3), 4.28 (m, 1H, H-2).

$^{13}$C NMR (CDCl$_3$): δ (ppm) 25.17, 26.77 (C-5, C-6), 47.49 (C-1), 66.55 (C-3), 73.70 (C-2), 110.29 (C-4), 132.76 (N=C=S).

b) Synthesis of 2-(3-{2-[3-(ditetradecyl-carbamoyl) propionylamino]-ethyl}-thioureido)-ethyl}-4-ylmethyl-2,2-dimethyl-[1,3]dioxalana (17)

Diisopropylethylamine (0.95 mmol, 0.165 ml) was directly added to the amine (9) (0.19 mmol, 0.146 g) obtained in the preceding stage and the reaction mixture was kept under stirring for 15 minutes. Then, $CH_2Cl_2$ (1.9 ml) and isothiocyanate (16) (0.209 mmol, 0.027 g) were added and the reaction mixture was left to react at room temperature under stirring for 12 hours. The mixture was then evaporated and purified by reverse phase liquid chromatography C8 with a gradient from 100% water to 100% acetonitrile. Product (17) was obtained in 49% yield.

$^1$H NMR (CDCl$_3$): δ (ppm) 0.88 (t, 6H, J=6.3 Hz, H-14'), 1.25 (m, 44 H, H-4'–H-11'), 1,34 et 1.43 (s, 3H, H-15, H-16), 1.48 (m, 4H, H-2'), 1.56 (m, 4H, H-3'), 2.52 (m, 2H, H-2), 2.68 (m, 2H, H-3), 3.23 (m, 4H, H-1'), 3.37 (m, 2H, H-5), 3.73 (m, 8H, H-6, H-8, H-9, H-11), 4.05 (m, 2H, H-13), 4.33 (m, 1H, H-12), 7.14 (4H, H thiourea).

$^{13}$C NMR (CDCl$_3$): δ (ppm) 14.06 (C-14'), 22.67 (C-13'), 25.32 (C-3'), 27.00 et 27.17 (C-15, C-16), 27.80 (C-2), 28.56

(C-2'), 28.84 (C-3), 29.66 (C-4'–C-11'), 31.25 (C-17), 31.92 (C-12'), 39.78 (C-5), 43.66 (C-6, C-8, C-9), 44.53 (C-11), 46.73 et 47.13(C-1'), 66.87 (C-136), 74.62 (C-12), 109.05 (C-14), 172.21 (C-1), 174.14 (C-4), 183.32 (C-7, C-10, C-13, C-16).

c) Synthesis of [2-(3-{2-[3-(ditetradecyl-carbamoyl)propionylamino]-ethyl}-thioureido)-ethyl]-propane-1,2-diol (DT-2TUdiol) (18)

X =

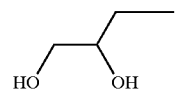

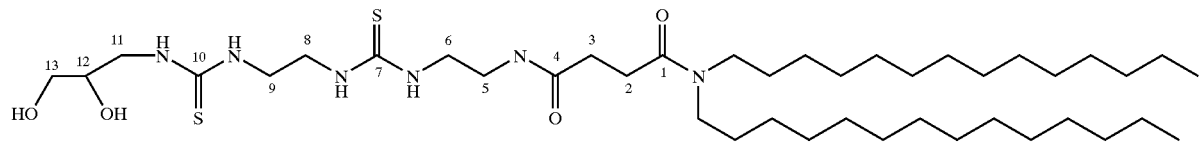

The protected diol (17) (0.05 g, 0.05 mmol) was dissolved in 1 mL of HCl 1N/THF (1/1) at room temperature and the reaction mixture was stirred for 18 hours. The reaction mixture was then extracted with dichloromethane (2×5 ml), the organic phases were mixed together and neutralised with sodium hydrogenocarbonate. The aqueous phases were extracted with dichloromethane. The organic phases were dried over magnesium sulphate and then the solvent was evaporated. The product obtained was purified by reverse phase liquid chromatography C8 with a gradient from 100% water to 100% acetonitrile. Product (18) was obtained in 49% yield.

$^1$H NMR (CDCl$_3$): δ (ppm) 0.88 (t, 6H, J=6.3 Hz, H-14'), 1.26 (m, 44 H, H-4'–H-11'), 1.43 (m, 4H, H-2'), 1.59 (m, 4H, H-3'), 1.79 (s, 2H, OH), 2.50 (m, 2H, H-2), 2.70 (m, 2H, H-3), 3.24 (m, 4H, H-1'), 3.39 (m, 2H, H-5), 3.72 (m, 6H, H-6, H-8, H-9), 3.9 (m, 2H, H-11), 4.22 (m, 2H, H-13), 4.58 (m, 1H, H-12), 7.14 (4H, H thiourea).

$^{13}$C NMR (CDCl$_3$): δ (ppm) 14.06 (C-14'), 22.67 (C-13'), 25.32 (C-3'), 27.80 (C-2), 28.56 (C-2'), 28.84 (C-3), 29.66 (C-4'–C-11'), 31.25 (C-17), 31.92 (C-12'), 39.78 (C-5), 43.66 (C-6, C-8, C-9), 45.86 (C-11), 46.73 et 47.13 (C-1'), 63.54 (C-13), 70.97 (C-12), 172.21 (C-1), 174.14 (C-4), 183.32 (C-7, C-10).

Example 4

Synthesis of DT-3TU diol

For the synthesis of DT-3TUdiol, amine (11) was used as the starting material.

The DT-3TU diol or Synthesis of {3-[2-(3-{2-[3-(2-{3-[2-(3-(ditetradecyl-carbamoyl)propionylamino)-ethyl]-thioureidoethyl}-thioureido]-ethyl}-thioureido)-ethyl}-propane-1,2-diol, is according to the general formula (I), wherein:

m=2
R=H
n=3
l=0;
Y=NH—CO—CH$_2$—CH$_2$; and
L=—N(R$_1$)R$_2$ where R$_1$=R$_2$=C$_{14}$H$_{29}$ a) Synthesis of 2-(3-{2-[3-(2-{3-[2-(3-(ditetradecyl-carbamoyl)propionylamino)-ethyl]-thioureido}-ethyl)-thioureido]-ethyl}-thioureido)-ethyl-4-ylmethyl-2,2-dimethyl-1,3]dioxalana (19)

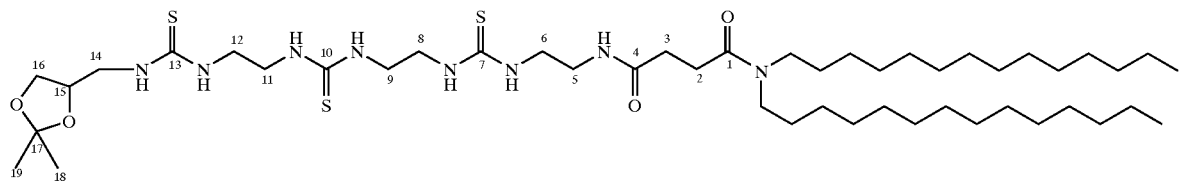

Diisopropylethylamine (0.95 mmol, 0.165 ml) was directly added to the amine (11) (0.19 mmol, 0.165 g) obtained in the preceding stage and the reaction mixture was kept under stirring for 15 minutes. Then, CH$_2$Cl$_2$ (1.9 ml) and isothiocyanate (16) (0.209 mmol, 0.027 g) were added and the reaction mixture was left to react at room temperature under stirring for 12 hours. The mixture was then evaporated and purified by reverse phase liquid chromatography C8 with a gradient from 100% water to 100% acetonitrile. Product (19) was obtained in 49% yield.

$^1$H NMR (CDCl$_3$): δ (ppm) 0.88 (t, 6H, J=6.3 Hz, H-14'), 1.25 (m, 44 H, H-4'–H-11'), 1.34 et 1.43 (s, 3H, H-18, H-19), 1.48 (m, 4H, H-2'), 1.56 (m, 4H, H-3'), 2.52 (m, 2H, H-2), 2.68 (m, 2H, H-3), 3.23 (m, 4H, H-1'), 3.37 (m, 2H, H-5), 3.73 (m, 12H, H-6, H-8, H-9, H-11, H-12, H-14), 4.05 (m, 2H, H-16), 4.33 (m, 1H, H-15), 7.14 (6H, H thiourea).

$^{13}$C NMR (CDCl$_3$): δ (ppm) 14.06 (C-14'), 22.67 (C-13'), 25.32 (C-3'), 27.00 et 27.17 (C-18, C-19), 27.80 (C-2), 28.56 (C-2'), 28.84 (C-3), 29.66 (C4'–C-11'), 31.25 (C-17), 31.92 (C-12'), 39.78 (C-5), 43.66 (C-6, C-8, C-9, C-11), 44.53 (C-14), 47.73 et 47.13(C-1'), 66.87 (C-16), 74.62 (C-15), 109.05 (C-17), 172.21 (C-1), 174.14 (C-4), 183.32 (C-7, C-10, C-13, C-16).

b) Synthesis of {3-[2-(3-{2-[3-(2-{3-[2-(3-(ditetradecyl-carbamoyl)propionylamino)-ethyl]-thioureido}ethyl)-thioureido]-ethyl}-thioureido)-ethyl}-propane-1,2-diol (DT-3TU diol) (20)

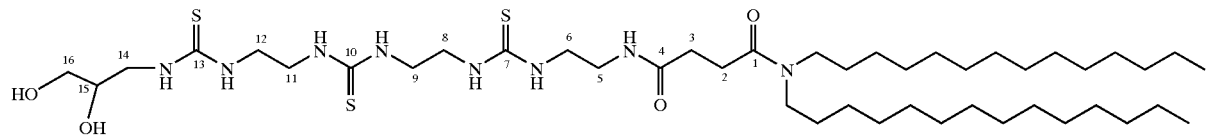

The protected diol (19) (0.05 g, 0.05 mmol) was dissolved in 1 mL of HCl 1N/THF (1/1) at room temperature and the reaction mixture was stirred for 18 hours. The reaction mixture was then extracted with dichloromethane (2×5 ml), the organic phases were mixed together and neutralised with sodium hydrogenocarbonate. The aqueous phases were extracted with dichloromethane. The organic phases were dried over magnesium sulphate and then the solvent was evaporated. The product obtained was purified by reverse phase liquid chromatography C8 with a gradient from 100% water to 100% acetonitrile. Product (18) was obtained in 55% yield.

$^1$H RMN (CDCl$_3$): δ (ppm) 0.88 (t, 6H, J=6.3 Hz, H-14'), 1.26 (m, 44 H, H-4'-H-11'), 1.43 (m, 4H, H-2'), 1.59 (m, 4H, H-3'), 1.79 (s, 2H, OH), 2.50 (m, 2H, H-2), 2.70 (m, 2H, H-3), 3.24 (m, 4H, H-1'), 3.39 (m, 2H, H-5), 3.72 (m, 10H, H-6, H-8, H-9, H-11, H-12), 3.9 (m, 2H, H-14), 4.22 (m, 2H, H-16), 4.58 (m, 1H, H-15), 7.14 (6H, H thiourea).

$^{13}$C RMN (CDCl$_3$): δ (ppm) 14.06 (C-14'), 22.67 (C-13'), 25.32 (C-3'), 27.80 (C-2), 28.56 (C-2'), 28.84 (C-3), 29.66 (C4'-C-11'), 31.25 (C-17), 31.92 (C-12'), 3.78 (C-5), 43.66 (C-6, C-8, C-9, C-11), 44.53 (C-14), 46.73 et 47.13(C-1'), 63.54 (C-16), 70.97 (C-15), 109.05 (C-17), 172.21 (C-1), 174.14 (C-4), 183.32 (C-7, C-10, C-13, C-16).

Example 5

Compaction of the Nucleic Acid in the Presence of DT-3TU (12)

The aim of this example is to illustrate the capacity of the transfecting compounds according to the invention to combine with the nucleic acids.

This can be easily demonstrated by a fluorescence test with ethidium bromide: the absence of fluorescence indicates the absence of free nucleic acid, which means that the nucleic acid was compacted by the transfecting compound.

The nucleic acid was brought into contact with increasing quantities of DT-3TU (12), by equivolumetric mixing of lipid solutions of various titers in the solutions of nucleic acid. Samples of 800 µl of nucleic acid complexes with a concentration of 0.01 µg/ml were thus prepared in a 150 mM sodium chloride solution with increasing quantities of DT-3TU (12).

In the same manner, a control was prepared by bringing the nucleic acid into contact with increasing quantities of EPC (see FIG. 1) or of DPPC (see FIG. 2), by equivolumetric mixing of lipid solutions of various titers in the solutions of nucleic acid. Samples of 800 µl of nucleic acid complexes with a concentration of 0.01 µg/mm were thus prepared in a 150 mM sodium chloride solution with increasing quantities of EPC or of DPPC (FIGS. 1 and 2 respectively).

The ethidium bromide fluorescence was measured over time (measured at 20° C.) using a FluoroMax-2 (Jobin Yvon-Spex) with excitation and emission wavelengths of 260 nm and 590 nm respectively. The slit widths for excitation and emission were set at 5 nm. The fluorescence value was recorded after addition of 3 µl of ethidium bromide to 1 g/l per ml of DNA/lipid solution (at 0.01 mg of DNA/ml).

Figure 1:
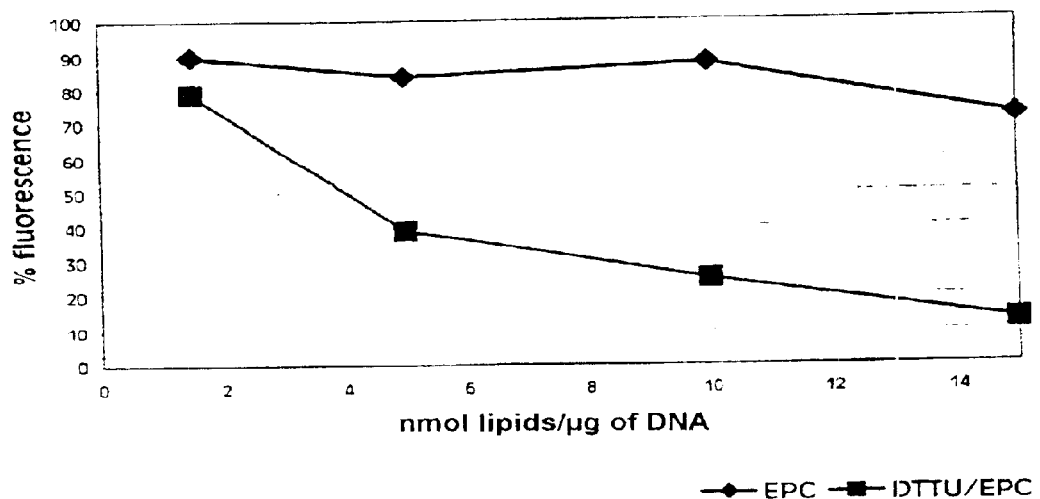
FIG. 1: Variation of the level of fluorescence (in %) as a function of the quantity of EPC/DTTU mixture (in nmol) per µg of nucleic acid and as a function of the quantity of EPC alone (in nmol) per µg of nucleic acid (control mixture).
Figure 2:
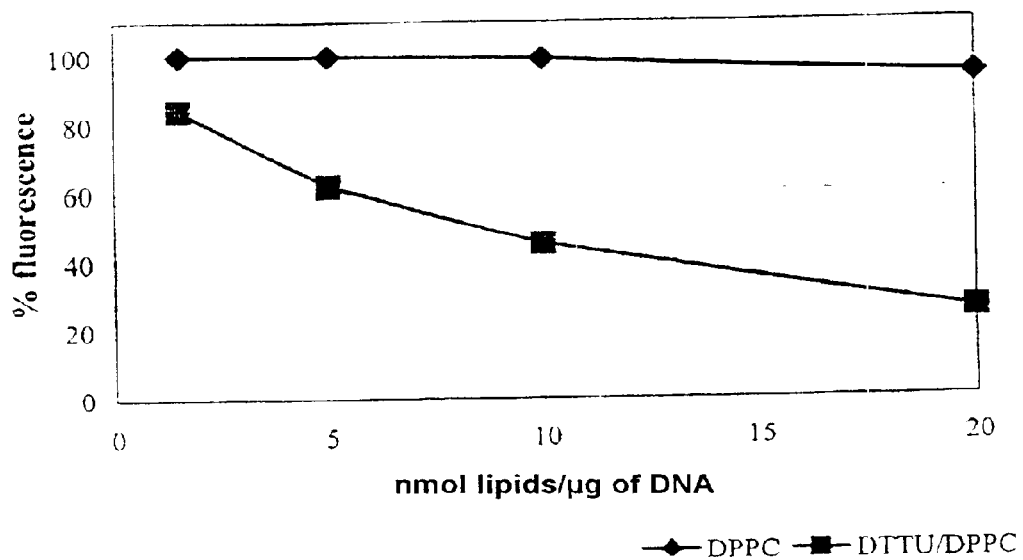
FIG. 2: Variation of the level of fluorescence (in %) as a function of the quantity of DPPC/DTTU mixture (in nmol) per µg of nucleic acid and as a function of the quantity of DPPC alone (in nmol) per µg of nucleic acid (control mixture).

The results were summarized in FIGS. 1 and 2.

In FIG. 1, the curve with squares shows that the addition of an increasing quantity of DT-3TU/EPC lipid mixture (0.75 to 20 nmol of DT-3TU) relative to a fixed quantity of nucleic acid (8 µg) induces a reduction in fluorescence linked to the reduction in the insertion of ethidium bromide between the base pairs of the DNA. This indicates that the combination between the DT-3TU/EPC liposomes and the DNA was sufficiently strong to exclude the ethidium bromide from the complexes. We were thus able to obtain up to 90% exclusion of fluorescence, that was 90% DNA-DT-3TU/EPC lipid combination. To show the active role of the DT-3TU lipid in this lipid/DNA combination, a control was prepared. It consists in observing the interaction between the EPC lipid and the DNA, this is represented by the curve with the diamonds. When the EPC was brought into contact with the DNA under conditions identical to those used for the study of the DT-3TU/EPC-DNA complexes, only a weak decrease in fluorescence was observed (about 5%), which may be attributed to the increase in the turbidity of the mixture. This control therefore reflects the absence of combination of EPC alone with the DNA under the abovementioned experimental conditions.

This example thus illustrates the capacity of the DT-3TU lipid to combine with the nucleic acid.

In the same manner, in FIG. 2, the curve with squares shows that the addition of an increasing quantity of DT-3TU/DPPC lipid mixture (0.75 to 20 nmol of DTTU) relative to a fixed quantity of nucleic acid (8 µg) induces a reduction in fluorescence when an identical quantity of ethidium bromide was added to the various samples. This indicates that the combination between the DT-3TU/DPPC liposomes and the DNA was sufficiently strong to exclude the ethidium bromide from the complexes. We were thus able to obtain up to 90% exclusion of fluorescence, that was 90% DNA-DTTU/DPPC combination. To show the active role of the DTTU lipid in this lipid/DNA combination, a control was prepared. It consists in observing the interaction between the DPPC lipid and the DNA, this is represented by the curve with the diamonds. When the DPPC was brought into contact with the DNA under conditions identical to those used for the study of the DT-3TU/DPPC-DNA complexes, only a weak decrease in fluorescence was observed (about 5%). This control therefore reflects the absence of the combination of DPPC alone with DNA under the abovementioned experimental conditions.

This example thus illustrates the capacity of the DT3-TU lipid to combine with the nucleic acid.

Example 6

Compaction of the DNA by DT-3TU/EPC Complexes

The aim of this example is to illustrate the capacity of the transfecting compounds according to the invention to compact the nucleic acids.

This may be easily demonstrated by a test of electrophoretic retardation on agarose gel of the DNA visualized by the use of ethidium bromide (EtBr): the absence of migration of the nucleic acid on the gel indicates the compaction of the nucleic acid. The free nucleic acid, for its part, was not subject to gel retardation.

Various DNA/DT-3TU samples comprising increasing quantities of DTTU lipid relative to the DNA were deposited on an agarose gel (0.8% agarose in 1N TBE). The gel was subjected to an electric current for one and a half hours at 70 V and 70 mA in order to cause the DNA to migrate by electrophoresis. The bands were revealed with EtBr and by absorption under a UV lamp. The results were represented in FIG. 3.

The gel shows the electrophoretic migration of the DNA when it was not combined with the lipids (well 1), and then its difference in retention when it was combined with the lipids. Wells 2 to 6 represent the DNA (0.01 g/l) combined with increasing quantities of DTTU/EPC liposomes: 0.75 then 5 then 10 then 15 and finally 20 nmol of DTTU lipid. Comparison between well 1 and the other wells indicates that the higher the increase in the quantity of DT-3TU lipid, the more DNA was retained on the gel which was completely retarded from 3 nmol of DTTU/$\mu$g of DNA, zone of aggregation of the complexes. Wells 8 to 13 correspond respectively to the DNA alone (0.1 g/l, 1 $\mu$g for the gel), the lipoplexes formed at the concentration of 0.1 g/l of DNA at the lipid/DNA ratios: 0.75 or 5 or 10 or 15 and finally 20 nmol/$\mu$g of DNA. In the same manner, it can be observed that at this concentration of DNA compatible with in vivo experiments, the DNA was compacted from ratios of 5 nmol lipid/$\mu$g of DNA.

This example thus illustrates the capacity of the DT-3TU lipid to compact the nucleic acid.

Example 7

Measurement of the Zeta Potential of the DT-3TU/DNA Compositions

The aim of this example is to illustrate the capacity of the transfecting compounds according to the invention to compact the nucleic acids while preserving a globally anionic, neutral or very weakly cationic structure.

This may be demonstrated by a measurement of the Zeta potential; the measurement given in mV indicates the surface charge of the particle relative to the electrophoretic mobility of the sample.

The nucleic acid was brought into contact with increasing quantities of the DT-3TU/EPC lipid mixture by equivolumetric mixing of lipid solutions of various titers in the solutions of nucleic acid. Samples of 2 ml of nucleic acid complexes with a concentration of 0.01 g/l were thus prepared in a 20 mM sodium chloride solution with increasing quantities of DT-3TU.

The measurement of the Zeta potential (mV) was carried out using a zetasizer 3000 Hsa (Malvern). The value of the potential was determined 3 times in succession on 2 ml of DT-3TU/EPC-DNA sample. The results were summarized in FIG. 4.

Figure 3:
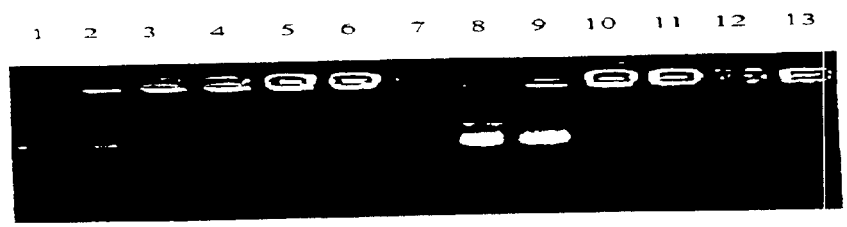
FIG. 3: Agarose gel (0.8%/TBE) showing the compaction of the plasmid pXL3031 (µg) as a function of the quantity of EPC/DTTU liposome (in nmol) used.

The DTTU/EPC liposomes were added to the DNA in a zone ranging from 0.75 nmol to 20 nmol of lipids per $\mu$g of DNA. In this zone of variation of the quantity of lipid, the Zeta potential varies from $-35$ mV to $+15$ mV. The negative part corresponds to what is shown in FIGS. 1, 2 and 3, namely that the Zeta potential was negative when the DNA was not completely compacted. The more lipid added, the more the DNA was compacted and the more the Zeta potential approaches zero, the lipoplexes then exhibit a practically zero surface potential. The Zeta potential then becomes slightly positive toward 8 nmol of lipid/$\mu$g of DNA. The relativity of this measurement should take into account the comparison of the various samples during the same experiment. It is thus important to note the evolution of the Zeta potential as a function of the increase in the quantity of lipid up to a weakly positive value.

This example thus confirms the compaction of the DNA by the transfecting compounds according to the invention, in particular DT-3TU, and show that the lipoplexes formed exhibit a surface potential close to neutrality.

Example 8

In vitro Transfection of the DT-3TU/DNA Compositions

The aim of this example is to illustrate the capacity of the transfecting compounds according to the invention to transfect cells in vitro.

This study was carried out for lipoplexes comprising various quantities of DT-3TU: 1.5 or 5 or 10 or 15 or 20 nmol of DT-3TU/$\mu$g of DNA. Each of these conditions was tested with and without fetal calf serum ("+Serum" or "−Serum").

The cell culture:

HeLa cells (American type Culture Collection (ATCC) Rockville, Md., USA) derived from a carcinoma of human cervical epithelium, were cultured in the presence of an MEM ("minimum essential medium") type medium with addition of 2 mM L-glutamine, 50 units/ml of penicillin and 50 units/ml of streptomycin. The medium and the additives were from Gibco-BRL Life Technologies (Gaithersburg, Md., USA). The cells were cultured in flasks at 37° C. and at 5% carbon dioxide in an incubator.

Transfection:

one day before the transfection, the HeLa cells were transferred into 240-well plates with a cell number of 30,000 to 50,000 per well. These dilutions represent approximately 80% confluence after 24 hours. For the transfection, the cells were washed twice and incubated at 37° C. with 500 $\mu$l of medium with serum (10% FCS v/v) or without serum. 50 $\mu$l of complexes containing 0.5 $\mu$g of plasmid DNA were added to each well (the complexes were prepared at least 30 minutes before addition to the wells). After 2 hours at 37° C., the plates without serum were supplemented with 10% (v/v) FCS ("Fetal Calf Serum").

All the plates were placed for 24 hours at 37° C. and at 5% carbon dioxide.

Determination of luciferase activity:

Briefly, the transfected cells were washed twice with 500 $\mu$l of PBS (phosphate buffer) and then lysed with 250 $\mu$l of reagent (Promega cell culture lysis reagent, of the Luciferase Assay System kit). An aliquot of 10 $\mu$l of supernatant of the lysate centrifuged (12,000×g) for 5 minutes at 4° C. was measured with a Wallace Victor 2 luminometer (1420 Multilabel couter). The luciferase activity was assayed by the light emission in the presence of luciferin, coenzyme A and ATP for 10 seconds and expressed relative to 2000 treated cells. The luciferase activity was then expressed in relative light units (RLU) and normalized with the concentration of proteins in the sample obtained using a Pierce BCA kit (Rockford, Ill., USA).

Figure 5:
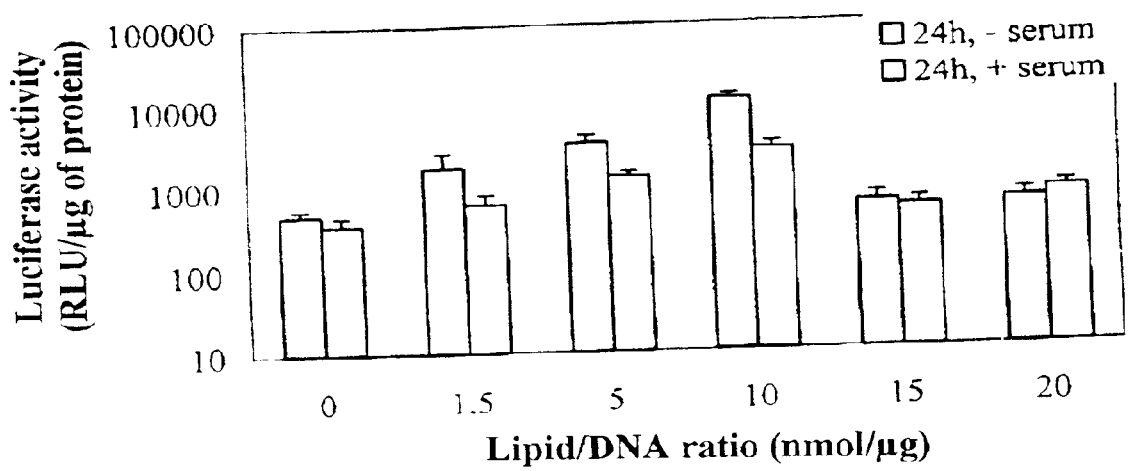
FIG. 5: Efficiency of in vitro transfection of HeLa cells with complexes formed between the DNA and the DTTU/DPPC (1:2) liposomes at various lipid/DNA ratios in nmol/µg, with or without serum.

The results summarized in FIG. 5 show an optimum transfection efficiency for the lipoplexes comprising 5 or 10 nmol of DT-3TU per µg of DNA. The presence of serum induces a weak inhibition of transfection in all cases.

Example 9

Determination of the Toxicity of the DTTU/DNA Lipoplexes Toward the Cells

The aim of this example is to illustrate the absence of toxicity of the transfecting compounds according to the invention.

The protein level was measured after transfection. The transfection protocol was identical to that described in Example 8.

Determination of the protein level:

Briefly, the transfected cells were washed twice with 500 µl of PBS (phosphate buffer) and then lysed with 250 µl of reagent (Promega cell culture lysis reagent, of the Luciferase Assay System kit). An aliquot of 50 µl of supernatant of the lysate centrifuged (12,000×g) for 5 minutes at 4° C. was transferred into a tube in the presence of 50 µl of 0.1 M iodoacetamide, 0.1 M hydrochloric acid tris at pH 8.2 and left for 1 hour at 37° C. 20 µl of the preceding solutions were deposited in a 96-well plate and 200 µl of "BCA protein assay" reagent (Pierce, Montluson, France) were added. The plate was then centrifuged at 2500 revolutions/min and then incubated at 37° C. for 30 minutes. In parallel, a bovine serum albumin (BSA) range was prepared in order to correlate the absorbance value obtained for the samples with a quantity of protein present in the sample.

The results summarized in FIG. 6 show a similar protein level regardless of the condition used, the lipoplexes comprising 0.75 or 5 or 10 or 15 or 20 nmol of DT-3TU per µg of DNA. The presence of DTTU lipid does not therefore adversely affect the cell and no toxicity was observed under the conditions used.

This example therefore illustrates one of the major advantages of the transfecting compounds according to the invention, namely their very low toxicity probably linked to the absence of positive charges in their structure.

Example 10

Compaction of the Nucleic Acid by DT-3TU/DPPC Nanoemulsions

The aim of this example is to illustrate the capacity of the transfecting compounds according to the invention to combine with the nucleic acids.

This may be easily demonstrated by a test of electrophoretic retardation on agarose gel of the DNA visualised by the use of ethidium bromide (EtBr): the absence of migration of the nucleic acid on the gel indicates the compaction of the nucleic acid. The free nucleic acid, for its part, is not subject to gel retardation.

Various DNA/DT-3TU samples comprising different formulations of DT-3TU lipid relative to the DNA were placed on an agarose gel (0.8% agarose in 1 N TBE). The gel is subjected to an electric current for one and a half hours at 70V and 40 mA in order to cause the DNA to migrate by electrophoresis. The bands were revealed with TBE and by absorption under a UV lamp. The results were presented in FIG. 8.

In the same way, the capacity of the DT-3TU diol compound to compact the DNA is shown by using an agarose gel (0.8% agarose in 1 N TBE), on which different samples of DNA/DT-3TU diol comprising different formulations of DT-3TUdiol lipid relative to the DNA were placed. The gel is subjected to an electric current for one and a half hours at 70V and 40 mA in order to cause the DNA to migrate by electrophoresis. The bands were revealed with ethidium bromide and by absorption under a UV lamp.

The gel shows the electrophoretic migration of the DNA when it is not combined with the lipids (well 1), and then its difference in retention when it is combined with the lipids. Wells 2 to 5 represent the DNA (0.01 g/l) combined with DT-3TU/DPPC (60 nmol DT-3TU/µg of DNA) nanoemulsions containing or not calcium and ethanol. Well 2 represents 60 nmol/µg of DNA without $Ca^{2+}$ and ethanol. In well 3, 2% of EtOH was added. In well 4, 60 eq. of $Ca^{2+}/PO^-$ DNA. In well 5, 2% of EtOH and 60 eq. of $Ca^{2+}$. Comparison between well 1 and the other wells indicates that the different DT-3TU formulations that were studied retard the DNA migration on the gel. The same result was observed after dialysis of $Ca^{2+}$ and EtOH.

This example illustrates thus the capacity of the DT-3TU lipid incorporated in different formulations to compact the nucleic acid.

Example 11

Compaction of the Nucleic Acid by Stabilised DT-3TU/DPPC Complexes

The aim of this example is to illustrate the capacity of the transfecting compounds according to the invention to combine with the nucleic acids.

This may be easily demonstrated by a test of electrophoretic retardation on agarose gel of the DNA visualised by the use of ethidium bromide (EtBr): the absence of migration of the nucleic acid on the gel indicates the compaction of the nucleic acid. The free nucleic acid, for its part, is not subject to gel retardation.

Various DNA/DT-3TU/DPPC and DNA/DT-3TUdiol/DPPC samples comprising increasing quantities of DT-3TU lipid relative to the DNA combined or not to the cholesterol-PEG were placed on an agarose gel (0.8% agarose in 1 N TBE). The gel was subjected to an electric current for one and a half hours at 70V and 40 mA in order to cause the DNA to migrate by electrophoresis. The bands were revealed with ethidium bromide and by absorption under a UV lamp. The results are shown in FIG. 9.

The use of cholesterol-PEG in the DT-3TU/DPPC formulations has the advantage of permitting the reduction of the particles to such a quantity of lipid that, in the case of the absence of lipid-PEG, would lead to aggregation. The interest in this result is to optimise the quantities of the transfecting compounds injected in vivo. In fact, the required size of the particles to have furtive objects towards the serum proteins should be manly inferior to 500 nm in order to have their half-life time increased in the blood stream. In order to obtain particles of this size it is necessary to use at least 40 nmol of the lipid DT-3TU/µg of DNA. Thus, the use of lipid-PEG in the formulations of the lipid DT-3TU has the advantage of reducing the quantity of DT-3TU necessary to compact the DNA and form particles whose size is smaller than 500 nm The gel shows the electrophoretic migration of the DNA when it is not combined with the lipids (well 1), and then its difference in retention when it is combined with the lipids. Wells 2 to 5 represent the DNA (0.01 g/l) combined with increased quantities of DT-3TU/DPPC nanoemulsions containing or not cholesterol-PEG (20 unites of ethylene glycol) as stabilising agent for the particles. Well 2 A represent 20 nmol/μg of DNA+15% of cholesterol-PEG. Well 3 contains 20 nmol/μg of DNA+20% of cholesterol-PEG. Well 4 represents 30 nmol/μg of DNA+15% of cholesterol-PEG and well 5 represents 20 nmol/μg of DNA+20% of cholesterol-PEG. Comparison between well 1 and the other wells indicates that the different DT-3TU formulations studied retard the DNA migration on the gel, showing the possibility of incorporating polymers of polyethylene glycol in these formulations without breaking free the DNA from the complexes and thus, without destabilising them.

This example illustrates thus the capacity of the DT-3TU lipid in the form of stabilised particles to compact the nucleic acid.

Example 12

Compaction of the Nucleic Acid in the Presence of DT-4TU (15)

The aim of this example is to illustrate the capacity of the transfecting compounds according to the invention to combine With the nucleic acids.

This can be easily demonstrated by a fluorescence test with ethidium bromide: the absence of fluorescence indicates the absence of free nucleic acid, which means that the nucleic acid was compacted by the transfecting compound.

The nucleic acid was brought into contact with increasing quantities of DT-4TU, by equivolumetric mixing of lipid solutions of various titers in the solutions of nucleic acid. Samples of 800 μl of nucleic acid complexes with a concentration of 0.01 μg/ml are thus prepared in a 150 mM solution of sodium chloride with increasing quantities of DT-4TU (15).

In the same manner, a control was prepared by bringing the nucleic acid into contact with increasing quantities of DT-3TU (12) by equivolumetric mixing of lipid solutions of different titers in the solutions of nucleic acid, to compare the efficiency of the complexion of a lipid containing 3 thioureas (see FIG. 2) with a lipid containing 4 thioureas. Samples of 800 μl of nucleic acid complexes with a concentration of 0.01 μg/ml are thus prepared in a solution of 5% glucose with increasing quantities of DPPC.

The ethidium bromide fluorescence was measured using a FluoroMax-2 (Jobin Yvon-Spex) with excitation and emission wavelengths of 260 nm and 590 nm respectively. The slit widths for excitation and emission are set at 5 nm. The fluorescence value was recorded after addition of 3 μl of ethidium bromide (1 g/l) per ml of DNA/lipid solution (0.01 g/l of DNA). The results are summarised in FIG. 10.

The curve with squares shows that the addition of an increasing quantity of DT-3TU/DPPC lipid mixture (0.75 to 30 nmoles of DT-3TU) relative to a fixed quantity of nucleic acid (8 μg) induces a reduction in fluorescence linked to the reduction of insertion of ethidium bromide between the base pairs of the DNA. This indicates that the combination between the liposomes DT-3TU/DPPC and the DNA was sufficiently strong to exclude the ethidium bromide from the complexes. We were thus able to obta0in 70% of the DNA compaction using 30 nmol of DT-3TU/DPPC lipids per μg of DNA. The active role of the DT-3TU in this lipids/DNA combination is shown in FIGS. 1 and 2. In the same manner, increasing quantities of DT4-TU/DPPC lipid mixture (0.75 to 30 nmoles of DT-3TU) were added to a fixed quantity of nucleic acid (8 μg). This combination induces a reduction in fluorescence linked to the reduction of insertion of ethidium bromide between the base pairs of the DNA. This indicates that the combination between the liposomes DT-4TU/DPPC and the DNA was sufficiently strong to exclude the ethidium bromide from the complexes. We were thus able to obtain 60% of the DNA compaction for 30 nmoles of lipid per μg of DNA (FIG. 10, curve with circles), which was similar to the efficiency of the DT-3TU complexion using the same conditions.

This example illustrates thus the capacity of the DT-4TU lipid to combine with the nucleic acid.

Example 13

Protection of the DNA from the DNAses by DT-3TU/DPPC Complexes

The aim of this example is to illustrate the capacity of the transfecting compounds according to the invention to protect the nucleic acids from enzymatic hydrolysis, namely the DNAses.

This may be easily demonstrated by a test of electrophoretic retardation on agarose gel of the DNA visualised by the use of ethidium bromide (EtBr). The free DNA or the DNA complexed with the lipid was treated with the right quantity of DNAse. The DNA was extracted from the enzymatic digestion mixture and was placed on an agarose gel. Its integrity was verified by comparison of its migration with that of the nucleic acid that had not been treated.

Various DNA samples, previously treated with $2.10^{-4}$ M of DNAse (Sigma), were placed on an agarose gel (0.8% agarose in 1 N TBE). Treatment with the DNAse was carried out on the free DNA and on the DNA complexed with increasing quantities of the DT-3TU lipid when compared with the DNA. The gel was subjected to an electric current for one and a half hours at 70V and 40 mA in order to cause the DNA to migrate by electrophoresis. The bands were revealed with ethidium bromide and by absorption under a UV lamp. The results are shown in FIG. 11.

The gel shows the electrophoretic migration of the DNA when it was not treated with the DNAse (well 1), and then its difference in retention after treatment. Well 2 represents the same quantity of DNA (3 μg) when treated with $2.10^{-4}$ M of DNAse. Following this treatment ($2.10^{-4}$ M of DNAse, 30 min. 37° C.), the corresponding band was not revealed, which indicates a degradation of the DNA. The nucleic acid complexed with 30 and 40 nmol of DT-3TU lipid per μg of DNA and with 40 nmol of DT-3TU lipid+6% of Chol-PEG was treated with $2.10^{-4}$ M of DNAse. After extraction of the DNA using a mixture of phenol/chloroform and its precipitation, the nucleic acid was placed on the agarose gel, respectively in wells 3, 4, and 5. The migration of the DNA was similar to the migration of the DNA that had not been treated previously with the DNAse. This indicates that the DNA was intact, that it has not been damaged by the treatment with DNAse and thus the DT-3TU lipid has protected it. The DNA in the DT-3TU lipid complexes was thus not accessible to the enzymatic hydrolysis, the nucleic acid was protected from the hydrolysis of the DNAses.

This example illustrates thus the capacity of the DT-3TU lipid to protect the nucleic acid from the enzymatic hydrolysis.

Example 14

Protection of the DNA from the Serum by the DT-3TU/DPPC Complexes

The aim of this example is to illustrate the capacity of the transfecting compounds according to the invention to protect the nucleic acids from degradation in the serum.

This may be easily demonstrated by a test of electrophoretic retardation on agarose gel of the DNA visualised by the use of ethidium bromide (EtBr). The free DNA or the DNA complexed with the lipid was incubated with different quantities of serum at 37° C. After its extraction from the serum, the DNA was placed on an agarose gel and its integrity was verified by comparison of its migration with that of the nucleic acid that had not been incubated.

Various DNA samples, previously incubated in 150 mM of NaCl, 20% and 100% of serum, were placed on an agarose gel (0.8% agarose in 1 N TBE). The saline and serum treatments were carried out with the free DNA and with the complexed DNA with increasing quantities of DT-3TU when compared with the DNA. The gel was subjected to an electric current for one and a half hours at 70V and 40 mA in order to cause the DNA to migrate by electrophoresis. The bands were revealed with ethidium bromide and by absorption under a UV lamp. The results are shown in FIG. 12.

The gel shows the electrophoretic migration of the DNA that was not treated (the blank) (well 1), then its difference in retention when the free DNA was treated in a saline solution (150 mM of NaCl) (well 2), when the DNA was complexed with 40 nmol of DT-3TU lipid per $\mu$g of DNA (well 3). The migration of the DNA extracted from the saline solution was similar in both wells. This indicates that the DNA was kept intact under these conditions. The following wells show in the same order the DNA (wells 4 and 6), the DNA+40 nmol of DT-3TU lipid (wells 5 and 7)in two different serum conditions: 20% of serum for the case of wells 4 to 5 and 100% of serum for the wells 6 to 7. When the DNA was free, the nucleic acid was completely degraded after 30 minutes at 37° C. (wells 4 and 6) under both the serum conditions mentioned previously. On the other hand, the DNA complexion with DT-3TU/DPPC nanoemulsions induces the protection of the nucleic acid since the migration band corresponding to the DNA was revealed (wells 5 and 7). The DNA in the DT-3TU lipid complexes was thus protected in the serum from degradation when compared with the free DNA.

This example illustrates thus the capacity of the DT-3TU lipid to protect the nucleic acid from degradation in the serum.

Example 15

In vivo Transfection of the DT-3TU/DNA Compositions

The aim of this example is to illustrate the capacity of the transfecting compounds according to the invention to transfect biological tissues in vivo.

This may be demonstrated by the intramuscular injection of the coding DNA complexes for the luciferase. Muscles samples were taken 96 hours after the injection and the level of expression for luciferase was measured using a luminometer (wallace).

Complexes containing increasing quantities of DT-3TU lipid per $\mu$g of DNA were injected in both tibial and cranial muscles of the mice, to which electric pulsations were or were not applied (Bureau, M et al, BBA 2000).

Complexes with increasing quantities of 40 and 60 mmol of DT-3TU lipid per $\mu$g of DNA were injected in a volume of 30 $\mu$L containing 3 $\mu$g of DNA per animal in both tibial and cranial muscles. The mice C57bl/6 had undergone previously anaesthetic with a mixture of Ketamin/Xylazine. The injection was or was not followed by the application of transcutaneous electric pulsations using electrodes placed in both ends of the muscle (Bureau, M et al, BBA 2000).

96 hours after the injection, the mice underwent euthanasia, muscles samples were taken and ground in 1 ml buffer lyse solution. After centrifugation (10 min., 12000 rpm, 4° C.), supernatant (10 $\mu$l) was taken and placed in a 96 well plate to read the luciferase after adding 50 $\mu$l of luciferase substrate. The level of luminescence was read in the supernatant using a luminometer (Wallace, Victor).

The results obtained are shown in FIG. 13. They represent the level of expression relative to the quantity of lipid combined with the nucleic acid, 20 and 40 nmol of DT-3TU lipid per $\mu$g of DNA. The different levels of expression that were obtained were significant and they were superior to the background noise that was obtained when the muscle was taken as a control ($5.0 \times 10^4$). The DNA complexed with different quantities of DT-3TU lipid was thus able to transfect the muscle tissues with a significant level of transfection.

This example illustrates the capacity of the transfecting compounds according to the invention to transfect tissues in vivo.

Example 16

In vivo Biodistribution of the DT-3TU/DPPC/DNA Complexes

The aim of this example is to illustrate the capacity of the transfecting compounds according to the invention to stay longer periods of time in the bloodstream in vivo due to their neutral character.

This may be demonstrated by the injection of the DNA complexes containing a fluorescent lipid in the mouse bloodstream. Blood samples were then taken at different times after the injection and the level of fluorescence in the bloodstream was measured using a FluoroMax-2 (Jobin Yvon-Spex).

Complexes containing 40 nmol of DT-3TU lipid per $\mu$g of DNA, 1 molar equivalent of DPPC/DT-3TU lipid and 0.7% of lipid-rhodamine (of the total amount of lipids) were injected in a volume of 200 $\mu$l containing 11 $\mu$g of DNA per animal in the caudal vein. The mice C57bl/6 had undergone anaesthetic with a mixture of Ketamin/Xylazine.

After the injection, blood samples were taken at 30 minutes, 1 hour and 6 hours by intracardiac puncture while the mice were anaesthetic. After euthanasia of the mice, the liver, the spleen and lungs were immediately extracted, weighed and homogenised in PBS (5 $\mu$l per mg of tissue). The lipids were extracted from 100 $\mu$L of blood and homogenised organs using 3 ml of chloroform/methanol mixture (1/1), by vigorously stirring for 30 minutes and then by centrifuge. The fluorescence in the supernatant was measured using a FluoroMax-2 (Jobin Yvon-Spex), with excitation and emission wavelengths of 550 nm and 590 nm respectively. The slit widths for excitation and emission were set at 5 nm.

Figure 4:
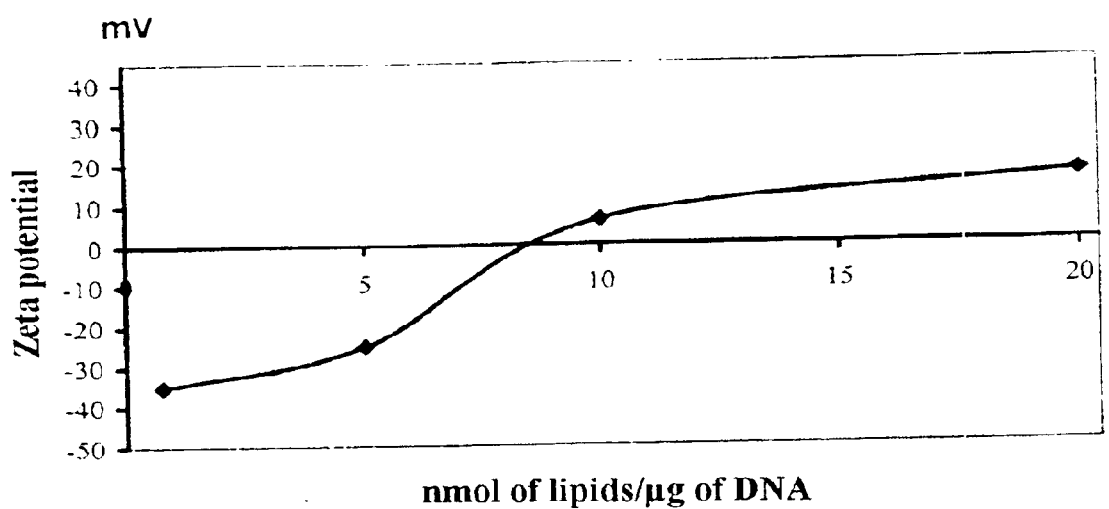
FIG. 4: Zeta potential (in mV) corresponding to the potential at the surface of the DPPC/DTTU-DNA liposomes as a function of the quantity of lipid (nmol) per µg of nucleic acid.

The results are summarised in FIG. 14. They represent the percentage of the dose injected obtained from the blood, lungs and the reticulo endothelial system (liver and spleen together) 30 minutes, 1 hour and 6 hours after injection. The measure of the fluorescence in the blood after 30 minutes represent 50% of the dose injected, which was much superior to what can be obtained with the DNA surfactant of the cationic type. After 1 hour, 17% of the dose injected could be detected, which still represents a remarkable improvement when compared with cationic complexes. The neutral character of these lipid/DNA complexes (zeta potential was very weakly positive: FIG. 4) represents thus a real advantage to obtain furtive particles towards the serum proteins. The neutral character should also restrict their interactions with the macrophages and the kupffer cells of the liver and spleen and this might explain the quantity of liposome found in the blood 30 minutes and 1 hour after the injection.

The quantity of lipoplexe found in the lungs was low compared with the quantity found when cationic lipoplexes were used. The neutrality of the liposomes should also decrease the non-specific interactions with the negative endothelium of the lungs.

This example illustrates the capacity of the transfecting compounds according to the invention to be furtive towards serum proteins.

What is claimed is:

1. A compound comprising a polythiourea group linked to a group

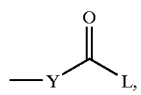

wherein

Y is a spacer;

and L is
—N(R$_1$)R$_2$ wherein R$_1$ and R$_2$ are, independently of each other, a hydrogen atom, a fatty aliphatic chain, or a group of formula —(CH$_2$)$_t$—OZ wherein t is 11, 12, 13, 14, or 15 and Z is a sugar, a polyol or a polyethylene glycol, wherein at least one of R$_1$ and R$_2$ is not a hydrogen atom;

or L is a group —OR$_3$, wherein R$_3$ is a steroid derivative.

2. A compound of formula (I):

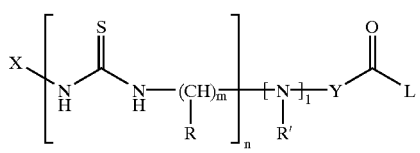

(I)

wherein:

l is 0 or 1;

n is 1, 2, 3, 4, 5, or 6;

m is 2, 3, or 4, wherein each m value is chosen independently for each group —[NH—CS—NH—(CH)$_m$]—, R' is a group of formula (II):

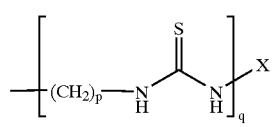

(II)

wherein q is 1, 2, 3, 4, 5, or 6, and p is 2, 3, or 4, wherein each p value is chosen independently for each group —[(CH$_2$)$_p$—NH—CS—NH]—;

R is either a hydrogen atom or a group of formula (II), wherein when n is 1 and l is 0, then at least one group R is of formula (II);

X, in the formulae (I) and (II), is a saturated or unsaturated, linear or cyclic aliphatic group, comprising 1 to 8 carbon atoms, a mercaptomethyl (—CH$_2$SH) group, a hydrophilic chain —(CHOH)$_u$—H where u is 1, 2, 3, 4, 5, or 6, or hydrophilic chain —(OCH$_2$CH$_2$O)$_v$—H where v is 1, 2, or 3, wherein no more than one substituent X, both in the formulae (I) and (II), is a hydrophilic chain;

Y is a spacer;

and L is
—N(R$_1$)R$_2$ wherein R$_1$ and R$_2$ are, independently of each other, a hydrogen atom, a fatty aliphatic chain, or a group of formula —(CH$_2$)$_t$—OZ wherein t is 11, 12, 13, 14, or 15 and Z is a sugar, a polyol or a polyethylene glycol, wherein at least one of R$_1$ and R$_2$ is not a hydrogen atom;

or L is a group —OR$_3$, wherein R$_3$ is a steroid derivative.

3. The compound according to claim 2, comprising formula (III):

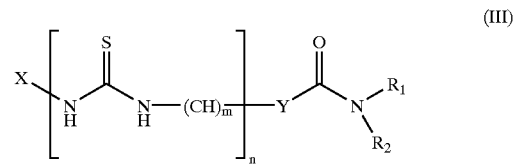

(III)

wherein X, m, n and Y are as defined in claim 2, with the proviso that n is not 1, and R$_1$ and R$_2$ are, independently of each other, a hydrogen atom or a fatty aliphatic chain, wherein at least one of R$_1$ and R$_2$ is not a hydrogen atom.

4. The compound according to claim 2, comprising formula (IV):

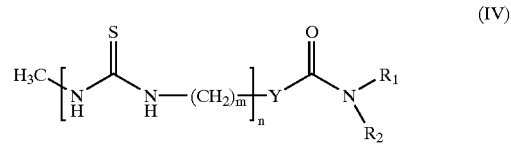

(IV)

wherein m, n and Y are as defined in claim 1, with the proviso that n is not 1, and R$_1$ and R$_2$ are, independently of each other, a hydrogen atom or a fatty aliphatic chain, wherein at least one of R$_1$ and R$_2$ is not a hydrogen atom.

5. The compound according claim 2, wherein said spacer comprises at least one chemical functional group chosen from alkyls having 1 to 6 carbon atoms, ketones, esters, ethers, amides, amidines, carbamate or thiocarbamate functional groups, glycerols, ureas, thioureas, or aromatic rings.

6. The compound according to claim 5, wherein Y is a group of formula (V) or formula (VI):

or:

wherein i and j are integers ranging from 1 to 6 and W is a ketone, ester, ether, amide, amidine, carbamate or thiocarbamate functional group, glycerol, urea, thiourea, or alternatively aromatic ring.

7. The compound according to claim 2, wherein group L comprises at least one fatty aliphatic chain chosen from an alkyl group comprising 10 to 22 carbon atoms and optionally at least one unsaturation.

8. The compound according to claim 7, wherein L comprises at least one fatty aliphatic chain chosen from aliphatic groups (CH$_2$)$_{11}$CH$_3$, (CH$_2$)$_{13}$CH$_3$, (CH$_2$)$_{15}$CH$_3$ and (CH$_2$)$_{17}$CH$_3$.

9. The compound according to claim 2, wherein $R_3$ is a steroid derivative chosen from polycyclic compounds of the cholestane type.

10. The compound according to claim 9, wherein said steroid derivative is cholesterol, cholestanol, 3-α-5-cyclo-5-α-cholestan-6-β-ol, cholic acid, cholesteryl formate, cholestanyl formate, 3α, 5-cyclo-5α-cholestan-6β-yl formate, cholesterylamine, 6-(1,5-dimethylhexyl)-3α,5α-dimethylhexadecahydrocyclopenta[a]cyclopropa[2,3]-cyclopenta[1,2-f]naphthalen-10-ylamine, or cholestanylamine.

11. The compound according to claim 2, wherein Z is a sugar comprising at least one saccharide.

12. The compound according to claim 2, wherein Z is a linear, branched or cyclic polyol comprising at least two hydroxyl functional groups.

13. The compound according to claim 2, wherein the compound of formula (I) is:

3-(2-{3-[2-(3-{2-[3-(ditetradecylcarbamoyl) propionylamino]ethyl}thioureido)ethyl]-thioureido}ethyl)-1-methylthiourea; or 3-(2-{3-[2-(3-{2-[3-(2-{3-[ditetradecyl-carbamoyl] propionylamino}-ethyl)-thioureido]-ethyl}-thioureido)-ethyl]-thioureido}-ethyl)-1-methylthiourea.

14. The compound according to claim 2, wherein
X=—CH$_2$CH(OH)CH$_2$(OH); m=2; R=H; n=3; l=0; Y=NH—CO—CH$_2$—CH$_2$; and L=—N(R$_1$)R$_2$ where R$_1$=R$_2$=C$_{14}$H$_{29}$.

15. The compound according to claim 2, wherein
X=—CH$_2$CH(OH)CH$_2$(OH); m=2; R=H; n=2; l=0; Y=NH—CO—CH$_2$—CH$_2$; and L=—N(R$_1$)R$_2$ where R$_1$=R$_2$=C$_{14}$H$_{29}$.

16. A composition comprising at least one nucleic acid and at least one compound comprising a polythiourea group linked to a group

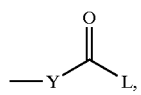

wherein
Y is a spacer;
and L is
—N(R$_1$)R$_2$ wherein R$_1$ and R$_2$ are, independently of each other, a hydrogen atom, a fatty aliphatic chain, or a group of formula —(CH$_2$)$_t$—OZ wherein t is 11, 12, 13, 14, or 15 and Z is a sugar, a polyol or a polyethylene glycol, wherein at least one of R$_1$ and R$_2$ is not a hydrogen atom;
or L is a group —OR$_3$, wherein R$_3$ is a steroid derivative.

17. A composition comprising at least one nucleic acid and at least one compound of formula (I):

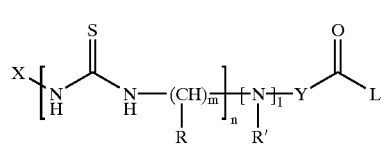

wherein:
l is 0 or 1;
n is 1, 2, 3, 4, 5, or 6;
m is 2, 3, or 4, wherein each m value is chosen independently for each group —[NH—CS—NH—(CH$_2$)$_m$]—,
R' is a group of formula (II):

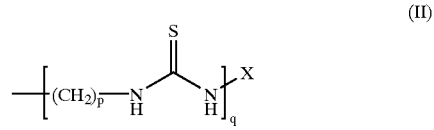

wherein q is 1, 2, 3, 4, 5, or 6, and p is 2, 3, or 4, wherein each p value is chosen independently for each group —[(CH$_2$)$_p$—NH—CS—NH]—;
R is either a hydrogen atom or a group of formula (II), wherein when n is 1 and l is 0, then at least one group R is of formula (II);
X, in the formulae (I) and (II), is a saturated or unsaturated, linear or cyclic aliphatic group, comprising 1 to 8 carbon atoms, a mercaptomethyl (—CH$_2$SH) group, a hydrophilic chain —(CHOH)$_u$—H where u is 1, 2, 3, 4, 5, or 6, or hydrophilic chain —(OCH$_2$CH$_2$O)$_v$—H where v is 1, 2, or 3, wherein no more than one substituent X, both in the formulae (I) and (II), is a hydrophilic chain;
Y is a spacer;
and L is
—N(R$_1$)R$_2$ wherein R$_1$ and R$_2$ are, independently of each other, a hydrogen atom, a fatty aliphatic chain, or a group of formula —(CH$_2$)$_t$—OZ wherein t is 11, 12, 13, 14, or 15 and Z is a sugar, a polyol or a polyethylene glycol, wherein at least one of R$_1$ and R$_2$ is not a hydrogen atom;
or L is a group —OR$_3$, wherein R$_3$ is a steroid derivative.

18. The composition according to claim 17, wherein said at least one nucleic acid is a deoxyribonucleic acid or a ribonucleic acid.

19. The composition according to claim 17, wherein said at least one nucleic acid comprises at least one gene of therapeutic interest under the control of at least one regulatory sequence.

20. The composition according to claim 17, wherein said at least one nucleic acid is an antisense gene or sequence or a DNA encoding an RNA with ribozyme functions.

21. The composition according to claim 17, further comprising at least one adjuvant.

22. The composition according to claim 21, wherein said adjuvant is a lipid, peptide, protein, polymer, or mixtures thereof.

23. The composition according to claim 22, wherein said polymer is polyethylene glycol covalently linked to cholesterol.

24. The composition according to claim 22, wherein said polymer is polyethylene glycol.

25. The composition according to claim 22, wherein said adjuvant comprises at least one neutral lipid.

26. The composition according to claim 25, wherein said neutral lipid is a natural lipid or synthetic lipid, wherein said lipid is zwitterionic or lacks an ionic charge while under physiological conditions.

27. The composition according to claim 25, wherein said neutral lipid is a dioleoylphosphatidylethanolamine (DOPE), oleoyl-palmitoylphosphatidylethanolamine (POPE), di-stearoylphosphatidylethanolamine, di-palmitoylphosphatidylethanolamine, di-myristoylphosphatidylethanolamine, or a derivative of any said phosphatidylethanolamine wherein said derivative is N-methylated 1, 2, or 3 times, a phosphatidylglycerol, a diacylglycerol, a glycosyldiacylglycerol, a cerebroside, a sphingolipid, or an asialoganglioside.

28. The composition according to claim 27, wherein said cerebroside is a galactocerebroside.

29. The composition according to claim 27, wherein said sphingolipid is a sphingomyelin.

30. The composition according to claim 27, wherein said asialoganglioside is an asialoGM1 or an asialoGM2.

31. The composition according to claim 17, further comprising at least one extracellular targeting element, or at least one intracellular targeting element, or a mixture thereof.

32. The composition according to claim 31, wherein said targeting element is a sugar, peptide, protein, oligonucleotide, lipid, neuromediator, hormone, vitamin, or a derivative thereof.

33. The composition according to claim 31, wherein said targeting element is covalently linked to a fatty alkyl chain comprising at least 10 carbon atoms or to a polyethylene glycol.

34. The composition according to claim 31, wherein said targeting element is covalently linked to said at least one nucleic acid or to said compound of formula (I).

35. The composition according to claim 17, further comprising a pharmaceutically acceptable vehicle for an injectable formulation.

36. The composition according to claim 17, further comprising a pharmaceutically acceptable vehicle for administration to the skin or the mucous membranes.

37. The composition according to claim 17, wherein the compound of formula (I) is:

3-(2-{3-[2-(3-{2-[3-(ditetradecylcarbamoyl) propionylamino]ethyl}thioureido)ethyl]-thioureido}ethyl)-1-methylthiourea; or
3-(2-{3-[2-(3-{2-[3-(2-{3-[ditetradecyl-carbamoyl] propionylamino}-ethyl)-thioureido]-ethyl}-thioureido)-ethyl]-thioureido}-ethyl)-1-methylthiourea.

38. The composition according to claim 17, wherein for said compound of formula (I):
X=—$CH_2CH(OH)CH_2(OH)$; m=2; R=H; n=3; l=0; Y=NH—CO—$CH_2$—$CH_2$; and L=—$N(R_1)R_2$ where $R_1=R_2=C_{14}H_{29}$.

39. The composition according to claim 17, wherein for said compound of formula (I):
X=—$CH_2CH(OH)CH_2(OH)$; m=2; R=H; n=2; l=0; Y=NH—CO—$CH_2$—$CH_2$; and L=—$N(R_1)R_2$ where $R_1=R_2=C_{14}H_{29}$.

40. A method for transferring nucleic acids into cells, comprising:
(A) forming a complex by contacting a nucleic acid with a compound according to claim 2; and
(B) contacting said cells with said complex.

41. The method for transferring nucleic acids into cells, according to claim 40, wherein said compound is:

3-(2-{3-[2-(3-{2-[3-(ditetradecylcarbamoyl) propionylamino]ethyl}thioureido)ethyl]-thioureido}ethyl)-1-methylthiourea; or
3-(2-{3-[2-(3-{2-[3-(2-{3-[ditetradecyl-carbamoyl] propionylamino}-ethyl)-thioureido]-ethyl}-thioureido)-ethyl]-thioureido}-ethyl)-1-methylthiourea.

42. The method for transferring nucleic acids into cells, according to claim 40, wherein said compound comprises:
X=—$CH_2CH(OH)CH_2(OH)$; m=2; R=H; n=3; l=0; Y=NH—CO—$CH_2$—$CH_2$; and L=—$N(R_1)R_2$ where $R_1=R_2=C_{14}H_{29}$.

43. The method for transferring nucleic acids into cells, according to claim 40, wherein said compound comprises:
X=—$CH_2CH(OH)CH_2(OH)$; m=2; R=H; n=2; l=0; Y=NH—CO—$CH_2$—$CH_2$; and L=—$N(R_1)R_2$ where $R_1=R_2=C_{14}H_{29}$.

44. A method for transferring nucleic acids into cells, comprising:
(A) forming a complex by contacting a nucleic acid with a compound comprising a polythiourea group linked to a group $$-Y \overset{O}{\underset{}{\overset{\|}{C}}} L,$$

wherein
Y is a spacer;
and L is
—$N(R_1)R_2$ wherein $R_1$ and $R_2$ are, independently of each other, a hydrogen atom, a fatty aliphatic chain, or a group of formula —$(CH_2)_t$—OZ wherein t is 11, 12, 13, 14, or 15 and Z is a sugar, a polyol or a polyethylene glycol, wherein at least one of $R_1$ and $R_2$ is not a hydrogen atom;
or L is a group —$OR_3$, wherein $R_3$ is a steroid derivative; and
(B) contacting said cells with said complex.

45. The method for transferring nucleic acids into cells according to claim 44, further comprising contacting said cells with at least one adjuvant.

46. The method for transferring nucleic acids into cells according to claim 44, further comprising contacting said cells at least one extracellular targeting element, or at least one intracellular targeting element, or mixtures thereof.

47. The method for transferring nucleic acids into cells according to claim 44, wherein said targeting element is a sugar, peptide, protein, oligonucleotide, lipid, neuromediator, hormone, vitamin, or derivative thereof.

48. The method for transferring nucleic acids into cells according to claim 44, wherein, before forming said complex, said compound comprising a polythiourea group linked to a group $$-Y \overset{O}{\underset{}{\overset{\|}{C}}} L$$

is admixed with at least one adjuvant.

49. The method for transferring nucleic acids into cells according to claim 44, wherein, before forming said complex, said nucleic acid is admixed with at least one adjuvant.

50. The method for transferring nucleic acids into cells according to claim 44, wherein, before forming said complex, said compound comprising a polythiourea group linked to a group $$-Y \overset{O}{\underset{}{\overset{\|}{C}}} L$$

is admixed with at least one extracellular targeting element, or at least one intracellular targeting element, or mixtures thereof.

51. The method for transferring nucleic acids into cells according to claim 44, wherein, before forming said complex, said nucleic acid is admixed with at least one extracellular targeting element, or at least one intracellular targeting element, or mixtures thereof.

52. The method for transferring nucleic acids into cells according to claim 44, wherein at least one adjuvant is administered to the cells before contacting said cells with said complex.

53. The method for transferring nucleic acids into cells according to claim 44, further comprising subjecting the cells to at least one chemical treatment, or at least one physical treatment, or a combination thereof.

54. A transfection kit, comprising at least one compound according to claim 2.

55. The transfection kit, according to claim 54, wherein said compound is:

3-(2-{3-[2-(3-{2-[3-(ditetradecylcarbamoyl) propionylamino]ethyl}thioureido)ethyl]- thioureido}ethyl)-1-methylthiourea; or 3-(2-{3-[2-(3-{2-[3-(2-{3-[ditetradecyl-carbamoyl] propionylamino}-ethyl)-thioureido]-ethyl}-thioureido)- ethyl]-thioureido}-ethyl)-1-methylthiourea.

56. The transfection kit, according to claim 54, wherein said compound comprises:

X=—CH$_2$CH(OH)CH$_2$(OH); m=2; R=H; n=3; l=0; Y=NH—CO—CH$_2$—CH$_2$; and L=—N(R$_1$)R$_2$ where R$_1$=R$_2$=C$_{14}$H$_{29}$.

57. The transfection kit, according to claim 54, wherein said compound comprises:

X=—CH$_2$CH(OH)CH$_2$(OH); m=2; R=H; n=2; l=0; Y=NH—CO—CH$_2$—CH$_2$; and L=—N(R$_1$)R$_2$ where R$_1$=R$_2$=C$_{14}$H$_{29}$.

58. A transfection kit, comprising at least one compound comprising a polythiourea group linked to a group

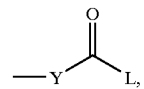

wherein

Y is a spacer;

and L is

—N(R$_1$)R$_2$ wherein R$_1$ and R$_2$ are, independently of each other, a hydrogen atom, a fatty aliphatic chain, or a group of formula —(CH$_2$)$_t$—OZ wherein t is 11, 12, 13, 14, or 15 and Z is a sugar, a polyol or a polyethylene glycol, wherein at least one of R$_1$ and R$_2$ is not a hydrogen atom;

or L is a group —OR$_3$, wherein R$_3$ is a steroid derivative.

* * * * *

UNITED STATES PATENT AND TRADEMARK OFFICE
CERTIFICATE OF CORRECTION

PATENT NO. : 6,812,218 B2
DATED : November 2, 2004
INVENTOR(S) : Jean Herscovici et al.

It is certified that error appears in the above-identified patent and that said Letters Patent is hereby corrected as shown below:

Column 36,
Lines 20-25, "

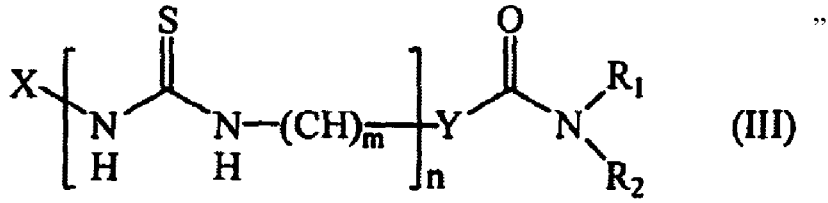

"

should read --

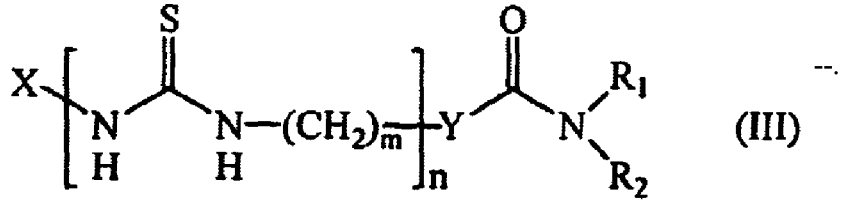

--.

Line 45, "according claim" should read -- according to claim --.

Column 38,
Line 24, "2, or3," should read -- 2, or 3, --.

Column 40,
Line 35, "cells at" should read -- cells with at --.

Signed and Sealed this

Twenty-eighth Day of March, 2006

JON W. DUDAS
*Director of the United States Patent and Trademark Office*